US008067161B2

(12) United States Patent
Ono et al.

(10) Patent No.: US 8,067,161 B2
(45) Date of Patent: Nov. 29, 2011

(54) DOPAMINERGIC NEURON PROLIFERATIVE PROGENITOR CELL MARKER NATO3

(75) Inventors: Yuichi Ono, Kyoto (JP); Yasuko Nakagawa, Kyoto (JP); Tomoya Nakatani, Kyoto (JP); Yoshimasa Sakamoto, Kyoto (JP)

(73) Assignee: Eisai R&D Management Co., Ltd., Tokyo-To (JP)

( * ) Notice: Subject to any disclaimer, the term of this patent is extended or adjusted under 35 U.S.C. 154(b) by 245 days.

(21) Appl. No.: 12/064,018

(22) PCT Filed: Aug. 18, 2006

(86) PCT No.: PCT/JP2006/316249
§ 371 (c)(1),
(2), (4) Date: Feb. 15, 2008

(87) PCT Pub. No.: WO2007/021003
PCT Pub. Date: Feb. 22, 2007

(65) Prior Publication Data
US 2010/0028866 A1 Feb. 4, 2010

(30) Foreign Application Priority Data

Aug. 18, 2005 (JP) ................. 2005-237759

(51) Int. Cl.
*C07H 21/04* (2006.01)
*C12Q 1/68* (2006.01)
(52) U.S. Cl. ........................ 435/6; 536/24.31
(58) Field of Classification Search ........................ None
See application file for complete search history.

(56) References Cited

U.S. PATENT DOCUMENTS

| | | | |
|---|---|---|---|
| 5,690,927 | A | 11/1997 | Major et al. |
| 6,277,820 | B1 | 8/2001 | Rosenthal et al. |
| 2005/0175997 | A1 | 8/2005 | Ono et al. |
| 2006/0239978 | A1 | 10/2006 | Nakagawa et al. |
| 2006/0240432 | A1 | 10/2006 | Ono et al. |
| 2007/0122882 | A1 | 5/2007 | Nakagawa et al. |
| 2007/0254281 | A1 | 11/2007 | Ono et al. |
| 2008/0280301 | A1 | 11/2008 | Ono et al. |
| 2010/0203505 | A1 | 8/2010 | Ono et al. |

FOREIGN PATENT DOCUMENTS

| | | |
|---|---|---|
| JP | 2002-51775 A | 2/2002 |
| WO | WO 94/23754 A1 | 10/1994 |
| WO | WO 95/12982 A1 | 5/1995 |
| WO | WO 96/14398 A1 | 5/1995 |
| WO | WO 96/14399 A1 | 5/1995 |
| WO | WO 96/14397 A1 | 5/1996 |
| WO | WO 96/28030 A1 | 9/1996 |
| WO | WO 96/28174 A1 | 9/1996 |
| WO | WO 96/39496 A1 | 12/1996 |
| WO | WO 97/02049 A1 | 1/1997 |
| WO | WO 99/43286 A2 | 9/1999 |
| WO | WO 99/56759 A1 | 11/1999 |
| WO | WO 99/64608 A1 | 12/1999 |
| WO | WO 00/06700 A1 | 2/2000 |
| WO | WO 00/09669 A1 | 2/2000 |
| WO | WO 01/57194 A2 | 8/2001 |
| WO | WO 02/074906 A2 | 9/2002 |
| WO | WO 02/103007 A1 | 12/2002 |
| WO | WO 2004/038018 A1 | 5/2004 |
| WO | WO 2004/065599 A1 | 8/2004 |
| WO | WO 2005/052190 A1 | 6/2005 |
| WO | WO 2007/021004 | 2/2007 |

OTHER PUBLICATIONS

Segev, E., et al., "Nato3 is an evolutionarily conserved bHLH transcription factor expressed in the CNS of *Drosophila* and mouse," *Mechanisms of Development*, vol. 106, pp. 197-202 (2001).
Guillemot, F., "Vertebrate bHLH Genes and the Determination of Neuronal Fates," *Experimental Cell Research*, vol. 253, pp. 357-364 (1999).
Kawasaki, H., et al., "Induction of Midbrain Dopaminergic Neurons from ES Cells by Stromal Cell-Derived Inducing Activity," *Neuron*, vol. 28, pp. 31-40 (Oct. 2000).
Kele, J., et al., "Function of proneural bHLH genes in ventral midbrain dopaminergic neurogenesis," *Mechanisms of Development; Abstracts of the 15th International Society of Developmental Biologists Congress 2005*, vol. 122 (Supplement 1), p. S181, Abstract 15—P021 (Jul. 12, 2005).
Verzi, M., et al., "N-Twist, an Evolutionarily Conserved bHLH Protein Expressed in the Developing CNS, Functions as a Transcriptional Inhibitor," *Developmental Biology*, vol. 249, pp. 174-190 (2002).
Wallén, A., et al., "Transcriptional Control of Dopamine Neuron Development," *Ann. N.Y. Acad. Sci.*, vol. 991, pp. 48-60 (Jun. 1, 2003).
PCT International Preliminary Report on Patentability (Chapter I) issued for PCT/JP2006/316249 on Feb. 28, 2008, 5 pgs.
Barberi, T., et al., "Neural subtype specification of fertilization and nuclear transfer embryonic stem cells and application in parkinsonian mice," *Nat. Biotechnol.*, vol. 21(10), pp. 1200-1207 (Oct. 2003).
Bjorklund, L. M., et al., "Embryonic stem cells develop into functional dopaminergic neurons after transplantation in a Parkinson rat model," *Proc. Nat'l Acad. Sci. U.S.A.*, vol. 99(4), pp. 2344-2349 (Feb. 19, 2002).
Defer, G. L., et al., "Long-term outcome of unilaterally transplanted parkinsonian patients," *Brain*, vol. 119, pt.1, pp. 41-50 (Feb. 1996).
Freed, C. R., et al., "Survival of implanted fetal dopamine cells and neurologic improvement 12 to 46 months after transplantation for Parkinson's disease," *N. Engl. J. Med.*, vol. 327(22), pp. 1549-1555 (Nov. 26, 1992).

(Continued)

Primary Examiner — John Ulm
(74) Attorney, Agent, or Firm — Kilpatrick Townsend & Stockton LLP

(57) ABSTRACT

The present invention is a probe, a primer, and an antibody, for detecting a dopaminergic neuron proliferative progenitor cell. According to the present invention, there is provided a polynucleotide probe and a polynucleotide primer for use in the detection or selection of a dopaminergic neuron proliferative progenitor cell, which can hybridize with a polynucleotide consisting of a nucleotide sequence of a Nato3 gene, or a complementary sequence thereto, and an antibody against a Nato3 protein, or a part thereof for use in the detection or selection of a dopaminergic neuron proliferative progenitor cell.

7 Claims, 6 Drawing Sheets

OTHER PUBLICATIONS

Hooper, J. D., et al., "Localization of the mosaic transmembrane serine protease corin to heart myocytes," *Eur. J. Biochem.*, vol. 267(23), pp. 6931-6937 (Dec. 2000).

Kawasaki, H., et al., "Generation of dopaminergic neurons and pigmented epithelia from primate ES cells by stromal cell-derived inducing activity," *Proc. Nat'l Acad. Sci. U.S.A.*, vol. 99(3), pp. 1580-1585 (Feb. 5, 2002).

Kim, J. H., et al., "Dopamine neurons derived from embryonic stem cells function in an animal model of Parkinson's disease," *Nature*, vol. 418(6893), pp. 50-56 (Jul. 4, 2002).

Kordower, J. H., et al., "Neuropathological evidence of graft survival and striatal reinnervation after the transplantation of fetal mesencephalic tissue in a patient with Parkinson's disease," *N. Engl. J. Med.*, vol. 332(17), pp. 1118-1124 (Apr. 27, 1995).

Lee, S. H., et al., "Efficient generation of midbrain and hindbrain neurons from mouse embryonic stem cells," *Nat. Biotechnol.*, vol. 18(6), pp. 675-679 (Jun. 2000).

Lindvall, O., et al., "Human Fetal Dopamine Neurons Grafted Into the Striatum in Two Patients With Severe Parkinson's Disease," *Aroh. Neurol.* vol. 46(6), pp. 615-631 (Jun. 1989).

Lopez-Lozano, J. J., et al., "Regression of Parkinsonian Fetal Ventral Mesencephalon Grafts Upon Withdrawal of Cyclosporine A Immunosuppression," *Transplant Proc.*, vol. 29(1-2), pp. 977-980 (Feb.-Mar. 1997).

Sakamoto, Y., et al., "The candidate of cell surface marker of dopaminergic progenitor cells," Proceedings of the 27th Annual meeting of the Molecular Biology Society of Japan, p. 762 (Nov. 25, 2004) 2PB-250.

Sawamoto, K., et al., "Generation of Dopaminergic Neurons in the Adult Brain from Mesencephalic Precursor Cells Labeled with a *nestin-GFP* Transgene," *J. Neurosci*, vol. 21(11), pp. 3895-3903 (Jun. 1, 2001).

Sawamoto, K., et al., "Visualization, direct isolation, and transplantation of midbrain dopaminergic neurons," *Proc. Nat'l Acad. Sci. U.S.A.*, vol. 98(11), pp. 6423-6428 (May 2001).

Selawry, H. P., et al., "Sertoli Cell-Enriched Fractions in Successful Islet Cell Transplantation," *Cell Transplant*, vol. 2(2), pp. 123-129 (1993).

Spencer, D. D., et al., "Unilateral Transplantation of Human Fetal Mesencephalic Tissue into the Caudate Nucleus of Patients with Parkinson's Disease," *N. Engl. J. Med.*, vol. 327(22), pp. 1541-1548 (Nov. 26, 1992).

Studer, L., et al., "Transplantation of expanded mesencephalic precursors leads to recovery in parkinsonian rats," *Nat. Neurosci.*, vol. 1(4), pp. 290-295 (1998).

Winder, H., et al., "Bilateral Fetal Mesencephalic Grafting in Two Patients with Parkinsonism Induced by 1-Methyl-4-Phenyl-1,2,3,6-Tetrahydropyridine (MPTP)," *N. Engl. J. Med.*, vol. 327(22), pp. 1556-1563 (Nov. 26, 1992).

Yan, W., et al., "Corin, a Mosaic Transmembrane Serine Protease Encoded by a Novel cDNA from Human Heart," *J. Biol. Chem.*, vol. 274(21), pp. 14926-14935 (May 21, 1999).

Yoshizaki, T., et al., "Isolation and transplantation of dopaminergic neurons generated from mouse embryonic stem cells," *Neurosci. Lett.*, vol. 363(1), pp. 33-37 (2004).

Zhao, S., et al., "Generation of embryonic stem cells and transgenic mice expressing green fluorescence protein in midbrain dopaminergic neurons," *Eur. J. Neurosci.*, vol. 19(5), pp. 1133-1140 (2004).

Japanese Office action dated Jul. 15, 2011, issued in related Japanese Patent Application No. 2007-531040.

Japanese Patent Application No. 2007-531041, entered Feb. 14, 2008, corresponding to U.S. Patent Publication No. 2010/203505, published Aug. 12, 2010 and published as WO 2007/021004 on Feb. 22, 2007.

MOUSE 12.5-DAY EMBRYO MIDBRAIN

DOPAMINERGIC NEURON PROLIFERATIVE PROGENITOR CELL MARKER NATO3

CROSS-REFERENCES TO RELATED APPLICATIONS

This application is a U.S. National Stage Application of PCT/JP2006/316249, filed Aug. 18, 2006, which claims the benefit of Japanese Application No. 2005-237759, filed Aug. 18, 2005.

TECHNICAL FIELD

The present invention relates to a Nato3 gene, which is a dopaminergic neuron proliferative progenitor cell marker. More particularly, the present invention relates to a means for detecting a dopaminergic neuron proliferative progenitor cell, a method for detecting the cell, and a kit for detecting the cell.

BACKGROUND ART

The dopamine system is a very important system involved in movement control, hormone secretion control, affectivity control, and so forth, which are important in the mammalian brain. Therefore, abnormalities in dopaminergic neurotransmission cause various disorders of the neural system. For example, the Parkinson's disease is a neurodegenerative disease of the extrapyramidal system which is caused by specific degeneration of dopaminergic neurons in the midbrain substantia nigra (HARRISON'S PRINCIPLES OF INTERNAL MEDICINE Vol. 2 $23^{rd}$ ed., Isselbacher et al. edited by McGraw-Hill Inc., NY (1994) pp. 2275-7).

As a method for treating the Parkinson's disease, a method of orally administering L-DOPA (3,4-dihydroxy-phenylalanine) has been mainly adopted for compensating the decrease in the amount of the produced dopamine, but it is known that the duration of the effect is not good.

Accordingly, as a method for compensating the loss of dopaminergic neurons, recently, there has been attempted a therapeutic method of transplanting a midbrain ventral region of a 6-9 week aborted fetus containing dopaminergic neuron precursors (U.S. Pat. No. 5,690,927; Spencer et al. (1992) N. Engl. J. Med. 327:1541-8; Freed et al. (1992) N. Engl. J. Med. 327:1549-55; Widner et al. (1992) N. Engl. J. Med. 327:1556-63; Kordower et al. (1995) N. Engl. J. Med. 332:1118-24; Defer et al. (1996) Brain 119:41-50; and Lopez-Lozano et al. (1997) Transp. Proc. 29:977-80). However, at the present time, in addition to cell supply and ethical issues (Rosenstain (1995) Exp. Neurol. 33:106; Turner et al. (1993) Neurosurg. 33:1031-7), various other problems have been indicated, for example, risk of infectious contamination, immunologic transplant rejection (Lopez-Lozano et al. (1997) Transp. Proc. 29:977-80 and Widner and Brudin (1988) Brain Res. Rev. 13:287-324), low survival rate due to the fetus tissue's mainly dependence on lipid metabolism rather than glycolysis (Rosenstein (1995) Exp. Neurol. 33:106), and so forth.

As a method for solving the problem of the ethical issues or supply shortage, for example, a method by using a cortex, a striation, and midbrain cells, derived from a pig, and so forth have been proposed (for example, Japanese Patent Laid-Open Publication No. 10-508487, No. 10-508488, and No. 10-509034). However, in this method, a complex procedure for modifying an antigen on the cell surface (MHC class I antigen) is required to suppress rejection. As a method for solving the transplant rejection, for example, a method involving local immunosuppression by simultaneously transplanting Sertoli cells has been proposed (Japanese Patent Laid-Open Publication No. 11-509170 and No. 11-501818; and Selawly and Cameron (1993) Cell Transplant 2:123-9). It is possible that transplant cells are obtained from a relative whose MHC matches, bone marrow of another person, a bone marrow bank, a cord blood bank, and so forth. However, if patient's own cells can be used, the problems of rejection can be solved without extra procedures and trouble.

Accordingly, it has been expected that, instead of cells derived from an aborted fetus, a differentiation system of dopaminergic neurons in vitro from non-neural cells such as embryo-stem (ES) cell and bone marrow stromal cells are utilized as a transplant material. Actually, there is a report that a functional dopaminergic neuron is formed by ES cell transplantation into lesion striation of a rat Parkinson's disease model (Kim et al. (2002) Nature 418:50-56). It is thought that in the future, importance of regenerative medicine from ES cells or the patient's own neural stem cells will increase.

On the other hand, in the treatment of damage of neural tissue, restructuring of brain function is required, and for forming appropriate linkage with surrounding cells (network formation), not mature cells but progenitor cells that can differentiate into neurons in vivo are required to be transplanted. However, in the transplantation of neuron progenitor cells, in addition to the above-described problem regarding supply, there is a problem that the progenitor cells can differentiate into a nonuniform cell population. For example, in the treatment of the Parkinson's disease, it is necessary that dopaminergic neurons are selectively transplanted among catecholamine-containing neurons. Before now, as transplant cells for use in the treatment of the Parkinson's disease, there has been proposed a striate body (Lindvall et al. (1989) Arch. Neurol. 46:615-31 and Widner et al. (1992) N. Engl. J. Med. 327:1556-63), an immortalized cell line derived from human embryonic nerve (Japanese Patent Laid-Open Publication No. 8-509215, No. 11-506930, and No. 2002-522070), a post-mitotic human neuron of NT2Z cells (Japanese Patent Laid-Open Publication No. 9-5050554), a neuron primordial cell (Japanese Patent Laid-Open Publication No. 11-509729), a cell transfected with an exogenous gene so as to produce catecholamine such as dopamine, a bone marrow stromal cell (Japanese Patent Laid-Open Publication No. 2002-504503 and No. 2002-513545), an ES cell in which a gene is modified (Kim et al. (2002) Nature 418:50-56), and so forth. However, none of these contain only dopaminergic neurons or cells to differentiate into dopaminergic neurons.

As a method for selectively condensing or isolating dopaminergic neurons from undifferentiated cell population, there has been proposed a method of, introducing a reporter gene expressing a fluorescent protein under control of promoter/enhancer of a gene such as tyrosine hydroxylase (TH) expressed in dopaminergic neurons into each cell of the cell population, isolating the cells emitting fluorescence, and thereby visualizing the alive dopaminergic neurons to condense, segregate or identify (Japanese Patent Laid-Open Publication No. 2002-51775). However, this method requires a complex step of introduction of an exogenous gene, and furthermore, when used in gene treatment, the existence of the reporter gene causes problem of toxicity and immunogenicity.

As described above, now, one of the largest problems in transplantation treatment for the Parkinson's disease is that the either dopaminergic neuron progenitor cells derived from the midbrain ventral region of aborted fetus or induced to differentiate are a mixture of various cells. It is desirable that only a desired cell species is isolated and used, considering safety in neural network formation. Furthermore, considering survival or ability for correctly forming a network in a brain in which the cells are transplanted, it can be said that it is desirable from the treatment effect that earlier proliferative progenitor cells are isolated and transplanted.

Before now, as a gene that selectively expresses in the dopaminergic neuron proliferative progenitor cells, Lrp4 (WO 2004/065599) has been reported. Additionally, some markers of dopaminergic neuron progenitor cells have been reported (WO 2004/038018 and WO 2004/052190). Among them, with respect to Lmx1a, expression has been confirmed in human and mouse dopaminergic neuron proliferative progenitor cells, postmitotic dopaminergic neuron precursor cells, and dopaminergic neurons (WO 2005/052190).

By the way, the Nato3 gene is a transcription factor having a basic helix-loop-helix (bHLH), and it has been reported that the Nato3 gene is expressed in the midbrain, and has an important role in the developmental process (Segev, E., N. Halachmi, A. Salzberg, and N. Ben-Arie. 2001. Mech Dev 106:197-202). Moreover, it has been reported that Nato3 is expressed in the midbrain, particularly, the most ventral side (floor plate), and relates to differentiation of neural cells (Verzi, M. P., J. P. Anderson, E. Dodou, K. K. Kelly, S. B. Greene, B. J. North, R. M. Cripps, and B. L. Black. 2002. Dev Biol 249:174-90).

However, it is not reported that Nato3 is selectively expressed in dopaminergic neuron proliferative progenitor cells.

SUMMARY OF THE INVENTION

The present inventors have recently found that a Nato3 gene (hereinafter, occasionally referred to as merely "Nato3") is selectively expressed in dopaminergic neuron proliferative progenitor cells. The present invention is based on this finding.

An object of the present invention is to provide a means for detecting a dopaminergic neuron proliferative progenitor cell, a method for detecting a dopaminergic neuron proliferative progenitor cell, and a kit for detecting a dopaminergic neuron proliferative progenitor cell.

Further, an object of the present invention is to provide a method for screening for a substance effective for inducing differentiation into dopaminergic neuron proliferative progenitor cells.

Furthermore, an object of the present invention is to provide a method for producing a dopaminergic neuron proliferative progenitor cell for use in the treatment of the Parkinson's disease.

The present invention provides a polynucleotide probe or polynucleotide primer for use in the detection or selection of a dopaminergic neuron proliferative progenitor cell, which can hybridize with a polynucleotide consisting of a nucleotide sequence of a Nato3 gene, or a complementary sequence thereto (hereinafter, occasionally referred to as "probe according to the present invention" or "primer according to the present invention").

The present invention provides an antibody against a Nato3 protein, or a part thereof for use in the detection or selection of a dopaminergic neuron proliferative progenitor cell (hereinafter, occasionally referred to as "antibody according to the present invention").

The present invention also provides a method for detecting or selecting a dopaminergic neuron proliferative progenitor cell, comprising the step of detecting expression of a Nato3 gene (hereinafter, occasionally referred to as "detection method according to the present invention").

The present invention further provides a kit for detecting or selecting a dopaminergic neuron proliferative progenitor cell comprising at least a probe according to the present invention, a primer according to the present invention, or an antibody according to the present invention.

The present invention provides a method for screening for a substance effective for inducing differentiation into a dopaminergic neuron proliferative progenitor cell, comprising the step of detecting expression of a Nato3 gene.

The present invention provides a method for producing a dopaminergic neuron proliferative progenitor cell for use in the treatment of the Parkinson's disease.

The present invention provides use of a polynucleotide that can hybridize with a polynucleotide consisting of a nucleotide sequence of a Nato3 gene, or a complementary sequence thereto, for detecting or selecting a dopaminergic neuron proliferative progenitor cell.

The present invention provides use of an antibody against a Nato3 protein, or a part thereof, for detecting or selecting a dopaminergic neuron proliferative progenitor cell.

The probe according to the present invention, the primer according to the present invention, and the antibody according to the present invention can be utilized as selective markers for dopaminergic neuron proliferative progenitor cells. Accordingly, the present invention is extremely useful in a purity test of a transplant material and development of a method for inducing differentiation into dopaminergic neuron proliferative progenitor cells in vitro, or the like, and is expected to contribute to the promotion of practical application of regenerative medicine.

DETAILED DESCRIPTION OF THE INVENTION

Figure 1:
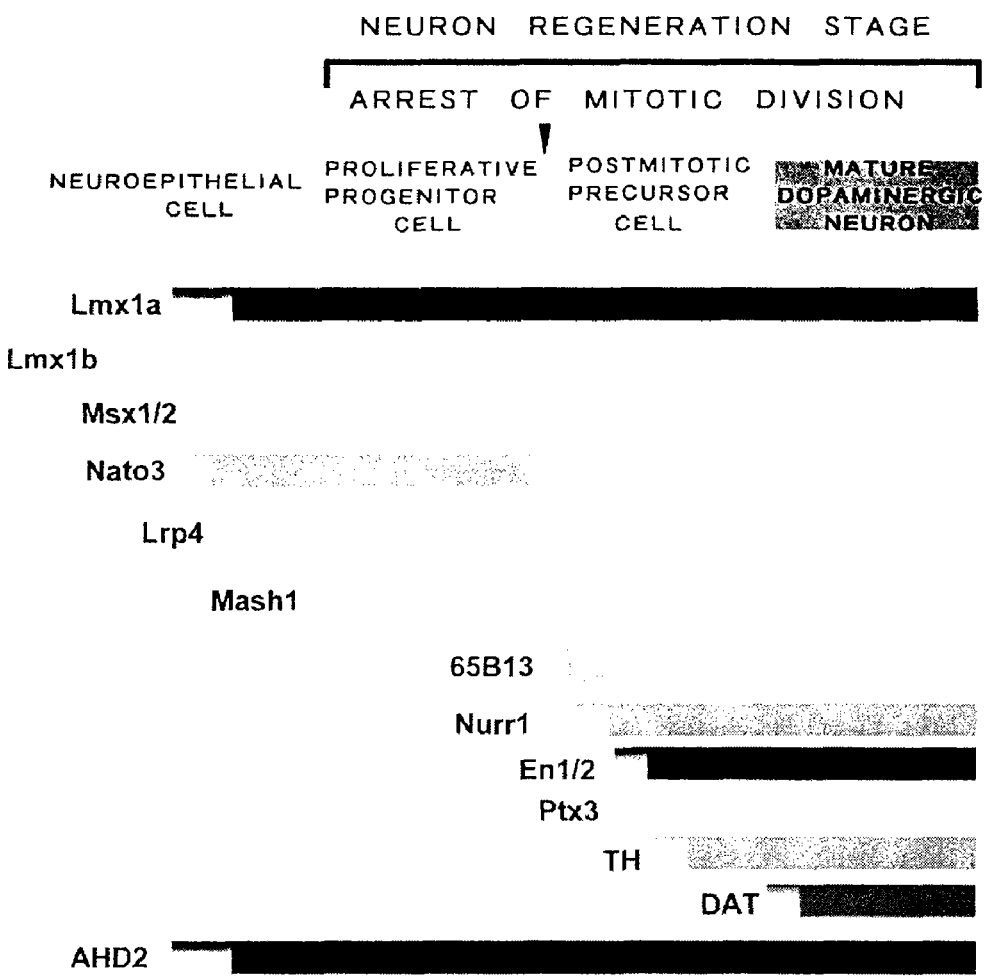
FIG. 1 shows an expression period of dopaminergic neurons-related marker genes.

Hereinafter, the present invention will be explained in detail. The following description is an example for explaining the present invention and the present invention is not limited to the embodiments to be described. All technical terms, scientific terms, and terminologies used in the present specification have the same meanings as those that are generally understood by those ordinary skilled in the art in the technical fields to which the present invention belongs and are used merely for the purpose of explanation of a specific embodiment but are not intended to make limitation. The present invention can be carried out in various embodiments as long as not departing from the spirit thereof. All the prior art documents, published publications, patent publications, and other patent documents, cited in the present specification, are incorporated into the present specification as references, and can be used for carrying out the present invention.

[Dopaminergic Neuron Proliferative Progenitor Cell]

The "dopaminergic neuron proliferative progenitor cell", which is an object to be detected or selected in the present invention, means a dopaminergic neuron progenitor cell before arrest of mitotic division.

The dopaminergic neuron differentiates from a neuroepithelial cell, through the differentiation stages of a proliferative progenitor cell and a postmitotic precursor cell, into a mature dopaminergic neuron. The dopaminergic neuron proliferative progenitor cell is the earliest progenitor cell in the dopaminergic neurons, and therefore, high survival rate and high ability of network formation in the brain to which the cell is transplanted can be expected. Therefore, the dopaminergic neuron proliferative progenitor cell is useful for transplantation therapy for diseases caused by decrease in dopamine due to degeneration of the dopaminergic neurons such as the Parkinson's disease.

The cells selected by using the probe, the primer, or the antibody according to the present invention as an index are dopaminergic neuron proliferative progenitor cells before arrest of mitotic division, and therefore, are preferable for the transplantation treatment for neurodegenerative diseases such as the Parkinson's disease in the aspects of safety, survival rate, and network formation ability, compared to a conventional mixed cell population or dopaminergic neuron progenitor cells in which an exogenous gene is introduced. The cells are dopaminergic neuron proliferative progenitor cells before arrest of mitotic division, namely, in proliferation, and have the possibility of differentiating to mature in the most appropriate place in the brain, and also, the dopaminergic neuron progenitor cells have the possibility of proliferating in vivo, and therefore, a longer effect of the treatment can be expected. Therefore, it can be said that the present invention paves the way to the practical application of the effective transplantation treatment of neurodegenerative diseases such as the Parkinson's disease.

[Polynucleotide Probe and Polynucleotide Primer]

The probe and the primer according to the present invention can hybridize specifically with a Nato3 gene. As described above, the expression of a Nato3 gene is useful as an index of dopaminergic neuron proliferative progenitor cells. Therefore, the probe or the primer according to the present invention can be used as a marker for detecting dopaminergic neuron proliferative progenitor cells.

The probe and the primer according to the present invention can be used for detecting expression of a Nato3 gene, and corresponds to a polymer consisting of a plurality of bases or base pairs such as deoxyribonucleic acid (DNA) or ribonucleic acid (RNA). It is known that double-strand cDNA can also be used in tissue in situ hybridization, and such double strand cDNA is included in the probe and the primer according to the present invention. As a particularly preferable probe and primer in detection of RNA in tissue, an RNA probe (riboprobe) can be exemplified.

The probe and the primer according to the present invention includes those consisting of a polynucleotide comprising a sequence of at least 10, preferably at least 15, more preferably at least 20, and further preferably at least 25 contiguous nucleotides of a nucleotide sequence of a Nato3 gene, or a complementary sequence thereto. Also, the probe and the primer according to the present invention includes those consisting of a polynucleotide comprising a sequence of 10-50 or 10-30, 15-50 or 15-30, 20-50 or 20-30, and 25-50 or 25-30 contiguous nucleotides of a nucleotide sequence of a Nato3 gene, or a complementary sequence thereto.

The probe and the primer according to the present invention can be at least 10 base length, preferably at least 15 base length, more preferably at least 20 base length, further preferably at least 25 base length. The probe and the primer according to the present invention can also be 10-50 base length or 10-30 base length, 15-50 base length or 15-30 base length, 20-50 base length or 20-30 base length, and 25-50 base length or 25-30 base length.

Preferable embodiments of the probe and the primer according to the present invention provide a probe and a primer having 15-30 base length for use in the detection or selection of a dopaminergic neuron proliferative progenitor cell, consisting of a polynucleotide comprising a sequence of at least 10 (preferably at least 15, more preferably at least 20, and further preferably at least 25) contiguous nucleotides of a nucleotide sequence of a Nato3 gene, or a complementary sequence thereto, which can hybridize with a Nato3 gene.

Preferable embodiments of the probe and the primer according to the present invention provide those that can hybridize with a high discrimination part in the nucleotide sequence of a Nato3 gene. By using such a probe and a primer, it becomes possible to detect the proliferative progenitor cells with higher accuracy. Such a probe and a primer include those that can hybridize with a nucleotide sequence comprising a part or all of a nucleotide sequence selected from the group consisting of nucleotides 1-365 and 534-640 of SEQ ID NO:1, nucleotides 1-376 and 545-662 of SEQ ID NO:3, nucleotides 1-306 and 475-501 of SEQ ID NO:5, nucleotides 1-377 and 546-886 of SEQ ID NO:7, nucleotides 1-312 and 481-507 of SEQ ID NO:9, nucleotides 1-306 and 475-501 of SEQ ID NO:11, nucleotides 1-306 and 475-501 of SEQ ID NO:13, nucleotides 1-177 and 346-372 of SEQ ID NO:15, nucleotides 1-359 and 528-557 of SEQ ID NO:17, nucleotides 1-357 and 523-552 of SEQ ID NO:19.

The probe according to the present invention can be used as a probe according to the general methods in known methods for detecting a gene of interest such as a northern blotting method, a southern blotting method, an in situ hybridization method, and so forth.

The probe according to the present invention can be chemically synthesized based on the nucleotide sequences disclosed in the present specification. The preparation of the probe is well-known and can be performed, for example, according to "Molecular Cloning, A Laboratory Manual $2^{nd}$ ed." (Cold Spring Harbor Press (1989)) and "Current Protocols in Molecular Biology" (John Wiley & Sons (1987-1997)).

The primer according to the present invention can also be used as a primer set consisting of two or more kinds of the primers.

The primer and the primer set according to the present invention can be utilized as a primer and a primer set according to the general methods in known methods for detecting a gene of interest by utilizing a nucleic acid amplification method such as a PCR method, a RT-PCR method, a real-time PCR method, an in situ PCR method, or a LAMP method.

The primer set according to the present invention can be selected so that the nucleotide sequence of a Nato3 gene can be amplified by a nucleic acid amplification method. Nucleic acid amplification methods are well-known, and selection of the primer pair in the nucleic acid amplification method is understood by those skilled in the art. For example, in the PCR method, primers can be selected so that one of the two primers (primer pair) is paired with the plus strand of the double strand DNA of a Nato3 gene, the other primer is paired with the minus strand of the double strand DNA, and with a strand extended by one primer, the other primer can be paired. Moreover, in the LAMP method (WO 00/28082), with respect to the target gene, three regions F3c, F2c, and F1c are defined from the 3' end side, and three regions B1, B2, and B3 are defined from the 5' end side, and by using the six regions, four kinds of primers can be designed.

The primer according to the present invention can be chemically synthesized based on the nucleotide sequences disclosed in the present specification. The preparation of the probe is well-known and can be performed, for example, according to "Molecular Cloning, A Laboratory Manual $2^{nd}$ ed." (Cold Spring Harbor Press (1989)), "Current Protocols in Molecular Biology" (John Wiley & Sons (1987-1997)).

In the present invention, the "Nato3 gene", which is an index of the existence of the dopaminergic neuron proliferative progenitor cell, is known in human, mouse, rat, chimpanzee, dog, bovine, chicken, and so forth. GenBank Accession Numbers disclosing the respective sequences are as follows.
Nato3 Gene
Human: NM_152898 (SEQ ID NO:1 (base sequence), SEQ ID NO:2 (amino-acid sequence), hereinafter representation will be in the same order), AF517122 (SEQ ID NO:3, SEQ ID NO:4), BC069147(SEQ ID NO:5, SEQ ID NO:6), AF369897 (same as BC069147)
Mouse: NM_033522(SEQ ID NO:7, SEQ ID NO:8), AF517121(same as NM_033522), AF369896(SEQ ID NO:9, SEQ ID NO:10)
Rat: XM_345658(SEQ ID NO: 11, SEQ ID NO: 12)
Chimpanzee: XM_527676(SEQ ID NO: 13, SEQ ID NO: 14)
Dog: XM_539457(SEQ ID NO:15, SEQ ID NO:16)
Bovine: XM_584097(SEQ ID NO: 17, SEQ ID NO: 18)
Chicken: XM_425989(SEQ ID NO:19, SEQ ID NO:20)

Also with respect to an animal (preferably mammal) except for the above-described animals, those skilled in the art can specify a sequence of a Nato3 gene inherent in the animal, based on the known full-length sequence of a Nato3 gene. For example, by homology search based on the human or mouse Nato3 gene, a Nato3 gene of the animal can be searched and identified. In the homology search, BLAST to be described later or the like can be used.

The Nato3 gene includes:
a polynucleotide encoding a human Nato3 protein consisting of an amino acid sequence of at least one selected from the group consisting of SEQ ID NO:2, SEQ ID NO:4, and SEQ ID NO:6;
a polynucleotide encoding a mouse Nato3 protein consisting of an amino acid sequence of at least one selected from the group consisting of SEQ ID NO:8 and SEQ ID NO:10;
a polynucleotide encoding a rat Nato3 protein consisting of an amino acid sequence of SEQ ID NO:12;
a polynucleotide encoding a chimpanzee Nato3 protein consisting of an amino acid sequence of SEQ ID NO:14;
a polynucleotide encoding a dog Nato3 protein consisting of an amino acid sequence of SEQ ID NO:16;
a polynucleotide encoding a bovine Nato3 protein consisting of an amino acid sequence of SEQ ID NO: 18; and
a polynucleotide encoding a chicken Nato3 protein consisting of an amino acid sequence of SEQ ID NO:20.

Moreover, the Nato3 gene includes:
a polynucleotide comprising a human Nato3 gene DNA sequence of at least one selected from the group consisting of SEQ ID NO:1, SEQ ID NO:3, and SEQ ID NO:5;
a polynucleotide comprising a mouse Nato3 gene DNA sequence of at least one selected from the group consisting of SEQ ID NO:7 and SEQ ID NO:9;
a polynucleotide comprising a rat Nato3 gene DNA sequence of SEQ ID NO:11;
a polynucleotide comprising a chimpanzee Nato3 gene DNA sequence of SEQ ID NO:13;
a polynucleotide comprising a dog Nato3 gene DNA sequence of SEQ ID NO:15;
a polynucleotide comprising a bovine Nato3 gene DNA sequence of SEQ ID NO: 17; and
a polynucleotide comprising a chicken Nato3 gene DNA sequence of SEQ ID NO:19.

The Nato3 gene according to the present invention includes genes encoding proteins which are functionally equivalent to a Nato3 protein. Whether the gene is "functionally equivalent" can be determined by evaluating a biological phenomenon or function relating to the expression of a Nato3 gene, for example, by evaluating whether the gene is selectively expressed in a dopaminergic neuron proliferative progenitor cell.

Moreover, the proteins which are functionally equivalent to a Nato3 protein include proteins having polymorphism when the gene encoding the amino acid sequence (such as amino acid sequence of SEQ ID NO:2) has polymorphism.

The gene encoding the proteins which are functionally equivalent to the Nato3 protein includes:
a gene encoding an amino acid sequence (modified amino acid sequence) of a Nato3 protein (for example, the amino acid sequence of SEQ ID NO:2 and the amino acid sequence of SEQ ID NO:8) in which one or more amino acid residues are inserted, substituted or deleted, or are added to one or both ends in the amino acid sequence;
a gene that can hybridize under stringent conditions with a gene encoding an amino acid sequence of a Nato3 protein (for example, the amino acid sequence of SEQ ID NO:2 and the amino acid sequence of SEQ ID NO:8); and
a gene encoding an amino acid sequence having at least an identity of 70% or more with an amino acid sequence of a Nato3 protein (for example, the amino acid sequence of SEQ ID NO:2 and the amino acid sequence of SEQ ID NO:8).

In the present specification, "one or more amino acid residues are inserted, substituted or deleted, or are added to one or both ends in the amino acid sequence" means that the modification is performed by a well-known technical method such as a site-directed mutagenesis or by substitution of a plurality of some amino acids to an extent of being naturally generated, or the like.

The modified amino acid sequence of a Nato3 protein can be an amino acid sequence in which, for example, 1-30, preferably 1-20, more preferably 1-9, further preferably 1-5, and particularly preferably 1 or 2 amino acid(s) is/are inserted, substituted, or deleted, or is/are added to one or both of end(s) in amino acid sequence. The modified amino acid sequence can be preferably an amino acid sequence having one or more (preferably, one or several, or 1, 2, 3 or 4) conservative substitutions in the amino acid sequence of the Nato3 protein.

The term "conservative substitutions" means that one or more amino acid residues are substituted with other chemically analogous amino acid residues so as not to substantially change protein activity. For example, the case that a certain hydrophobic residue is substituted with another hydrophobic residue and the case that a certain polar residue is substituted with another polar residue having the same charge can be exemplified. Functionally analogous amino acids which can be substituted in such a manner are known in the technical field, with respect to every amino acid. To give specific examples, the non-polar (hydrophobic) amino acid includes alanine, valine, isoleucine, leucine, proline, tryptophan, phenylalanine, methionine. The polar (neutral) amino acid includes glycine, serine, threonine, tyrosine, glutamine, asparagines, cysteine. Positively charged (basic) amino acids include arginine, histidine, and lysine. Moreover, negatively charged (acidic) amino acids include aspartic acid and glutamic acid.

In the present specification, "hybridize" means hybridization to a target polynucleotide under stringent conditions. Specifically, there can be exemplified a polynucleotide having identity of at least 70% or more, preferably 80% or more, more preferably 85% or more, further preferably 90% or more, further more preferably 95% or more, particularly preferably 98% or more, and most preferably 99% or more, with the target nucleotide sequence when calculation is performed using a parameter of default (initial setting) with homology search software such as FASTA, BLAST, Smith-Waterman [Meth. Enzym., 164, 765 (1988)]. Moreover, "under stringent conditions" can be performed according to a method of performing reaction in a hybridization buffer solution that can be generally used by those skilled in the art so that the temperature is 40-70° C., and preferably 60-65° C. and performing rinsing in a rinse solution whose salt concentration is 15-300 mmol/L, and preferably 15-60 mmol/L. The temperature and the salt concentration can be appropriately adjusted according to length of the probe to be used. Furthermore, the condition when the hybridized nucleotide is rinsed can be 0.2 or 2×SSC, 0.1% SDS, and a temperature of 20-68° C. As to control of the stringent conditions (high stringency) or the mild condition (low stringency), the difference can be provided by salt concentration or temperature in rinsing. When the difference of the hybridization is provided by salt concentration, a stringent wash buffer (high stringency wash buffer) of 0.2×SSC and 0.1% SDS can be used, and a mild wash buffer (low stringency wash buffer) of 2×SSC and 0.1% SDS. Moreover, when the difference of the hybridization is provided by temperature, the temperature is 68° C. in the stringent case, 42° C. in the case of moderate stringency, and room temperature (20-25° C.) in the mild case, and every case thereof may be performed under 0.2×SSC and 0.1% SDS.

In general, the prehybridization is performed under the same conditions as the hybridization. However, hybridization and preliminary rinsing are not limited to be performed under the same conditions.

The hybridization can be performed according to a known method. Moreover, in the case of using a commercially available library, the hybridization can be performed according to the method described in the appended instruction for use.

In the present specification, the term "identity" (occasionally referred to as homology) with respect to amino acid sequences means the degree of identity of the amino acid residues of the respective sequences between the sequences to be compared. In this case, existence of a gap and property of the amino acid are considered (Wilbur, Natl. Acad. Sci. U.S.A. 80:726-730 (1993)). For calculation of the homology, BLAST (Altschul: J. Mol. Biol. 215:403-410 (1990)), FASTA (Peasron: Methods in Enzymiology 183:63-69 (1990)), or the like can be used.

The amino acid sequence having at least an identity of 70% or more with the amino acid sequence of a Nato3 protein can be an amino acid sequence having identity of preferably 80% or more, more preferably 85% or more, further preferably 90% or more, further more preferably 95% or more, particularly preferably 98% or more, and most preferably 99% or more.

The "identity" may be a value calculated by using a homology search program known by those skilled in the art and can be calculated, for example, by using a parameter of default (initial setting) in the homology algorithm BLAST(Basic local alignment search tool) ncbi.nlm.nih.gov/BLAST/ in NCBI (National Center for Biotechnology Information).

[Antibody]

The antibody according to the present invention can recognize specifically a Nato3 protein. As described above, the expression of a Nato3 gene is useful as an index for dopaminergic neuron proliferative progenitor cells. Therefore, the antibody according to the present invention can be used as a marker for detecting dopaminergic neuron proliferative progenitor cells.

A Nato3 protein for obtaining the antibody according to the present invention may have antigenicity of Nato3 and includes a protein in which one or more amino acid residues are deleted, inserted, substituted, or added in an amino acid sequence of a Nato3 protein. It is known that in such a protein, the same biological activity as the original protein is maintained (Mark et al. (1984) Proc. Natl. Acad. Sci. USA 81:5662-6; Zoller and Smith (1982) Nucleic Acids Res. 10:6487-500; Wang et al. (1984) Science 224:1431-3; and Dalbadie-McFarland et al. (1982) Proc. Natl. Acad. Sci. USA 79:6409-13). A method that one or more amino acid residues are deleted, inserted, substituted, or added in the state of maintaining the antigenicity of the original protein in a protein is known. For example, a polynucleotide encoding a mutant protein can be prepared by a site-directed mutagenesis and can be appropriately expressed (Molecular Cloning, A Laboratory Manual $2^{nd}$ ed., Cold Spring Harbor Press (1989), Current Protocols in Molecular Biology, John Wiley & Sons (1987-1997); Sections 8.1-8.5; Hashimoto-Goto et al. (1995) Gene 152:271-5; Kinkel (1985) Proc. Natl. Acad. Sci. USA 82:488-92; Kramer and Fritz (1987) Method. Enzymol. 154: 350-67; and Kunkel (1988) Method. Enzymol. 85:2763-6).

The antibody according to the present invention includes an antibody specific to a part of a Nato3 protein. Specifically, a Nato3 protein for obtaining an antibody of the present invention includes a polypeptide fragment having at least 6 amino acid residues or more (for example, 6, 8, 10, 12, or 15 amino acid residues or more) of the Nato3 protein, as well as a polypeptide having a full-length amino acid sequence. The polypeptide fragment of the Nato3 protein in the present specification includes every fragment as long as the fragment has antigenicity of the Nato3 protein.

The preferable fragment includes polypeptide fragments such as the amino terminal or the carboxyl terminal of the Nato3 protein. The antigenic determinant site of the polypeptide is estimated by a method of analyzing hydrophobicity/ hydrophilicity of the amino acid sequence of the protein (Kyte-Doolittle(1982) J. Mol. Biol. 157:105-22) or a method of analyzing the secondary structure (Chou-Fasman (1978) Ann. Rev. Biochem. 47:251-76), and furthermore, confirmed by a computer program (Anal. Biochem. 151:540-6 (1985)) or a technique such as a PEPSCAN method (Japanese Patent Laid-Open Publication No. 60-500684) of synthesizing a short peptide and confirming the antigenicity.

The antibody against the Nato3 protein includes:

an antibody against a protein having an amino acid sequence of at least one selected from the group consisting of SEQ ID NO:2, SEQ ID NO:4, and SEQ ID NO:6, or a part thereof;

an antibody against a protein having an amino acid sequence of at least one selected from the group consisting of SEQ ID NO:8 and SEQ ID NO:10, or a part thereof;

an antibody against a protein having an amino acid sequence of SEQ ID NO: 12, or a part thereof;

an antibody against a protein having an amino acid sequence of SEQ ID NO: 14, or a part thereof;

an antibody against a protein having an amino acid sequence of SEQ ID NO: 16, or a part thereof;

an antibody against a protein having an amino acid sequence of SEQ ID NO: 18, or a part thereof; and an antibody against a protein having an amino acid sequence of SEQ ID NO: 20, or a part thereof.

Preferable embodiments of the antibody according to the present invention provide an antibody recognizing a high discrimination polypeptide portion in a Nato3 protein. By using such an antibody, it becomes possible that the proliferative progenitor cells can be detected with higher accuracy. Such antibody includes an antibody against a high discrimination polypeptide portion in a Nato3 protein, for example, at least 6 amino acid residues or all of an amino acid sequence selected from a group consisting of amino acids 1-102 and 159-166 of SEQ ID NO:2, amino acids 1-102 and 159-166 of SEQ ID NO:4, amino acids 1-102 and 159-166 of SEQ ID NO:6, amino acids 1-104 and 161-168 of SEQ ID NO:8, amino acids 1-104 and 161-168 of SEQ ID NO:10, amino acids 1-102 and 159-166 of SEQ ID NO:12, amino acids 1-102 and 159-166 of SEQ ID NO:14, amino acids 1-59 and 116-123 of SEQ ID NO:16, amino acids 1-101 and 158-164 of SEQ ID NO:18, amino acids 1-119 and 176-183 of SEQ ID NO:20.

The antibody according to the present invention can also be obtained by using a well-known method for those skilled in the art (for example, "Current Protocols in Molecular Biology" (John Wiley & Sons (1987) and Antibodies: A Laboratory Manual, Ed. Harlow and David Lane, Cold Spring Harbor Laboratory (1988).

The antibody according to the present invention includes a polyclonal antibody, a monoclonal antibody, a chimeric antibody, a single-strand antibody (scFv), a humanized antibody, a polyspecific antibody, and antibody fragments such as Fab, Fab', $F(ab')_2$, Fc, and Fv.

In the case of the polyclonal antibody, the blood of a mammal in which an antigen is sensitized is extracted and serum is segregated from the blood by a known method to serve as the serum containing the polyclonal antibody.

According to need, fractions containing the polyclonal antibodies can also be further isolated.

In the case of the monoclonal antibody, antibody-producing cells obtained from the spleen or the lymph node of a mammal in which the above-described antigen is sensitized are extracted and cell-fused with myeloma cells. The obtained hybridoma is cloned and the antibody is collected from the culture to serve as the monoclonal antibody.

As the immunizing antigen, a fragment of the Nato3 protein can be used. Alternatively, an antigen synthesized based on the above-described amino acid sequence can be used. The antigen may be used as a complex with a carrier protein. For preparation of the complex of the antigen and the carrier protein, various condensation agents such as glutaraldehyde, carbodiimide, maleimide-activated ester, or the like can be used. The carrier protein may be one generally used such as bovine serum albumin, thyroglobulin, hemocyanin, or the like and is generally performed coupling at a ratio of 1-5.

The animal to be immunized includes mouse, rat, rabbit, guinea pig, and hamster. The injection method includes subcutaneous, muscular, or intraperitoneal administration. In the administration, the antigen may be mixed with complete Freund's adjuvant or incomplete Freund's adjuvant. The administration is generally performed one time per 2-5 weeks.

The antigen-producing cells obtained from the spleen or the lymph node of the immunized animal is cell-fused with myeloma cells and isolated as hybridomas. The myeloma cells derived from mouse, rat, or human are used, and are preferably derived from the same species as the antigen-producing cells, but cells between different species are occasionally possible.

The cell fusion can be performed according to a previously known method, for example, the method disclosed in Nature, 256, 495, 1975.

The fusion accelerator includes polyethylene glycol or Sendai virus, and in general, the cell fusion can be performed by reaction for approximately 1-10 minutes so that the ratio of the number of the antigen-producing cells and the number of the myeloma cells is generally approximately 1:1-10:1, under a temperature of 20-40° C., and preferably 30-37° C. by using polyethylene glycol (average molecular weight 1000-4000) having a concentration of approximately 20-50%.

For the screening of the antigen-producing hybridoma, various immunochemical methods can be used. For example, an ELISA method in which a microplate on which the Nato3 protein is coated is used, an EIA method in which a microplate on which an anti-immunoglobulin antibody is coated is used, and an immunoblotting method in which a nitrocellulose transfer membrane is used after electrophoresing samples containing the Nato3 protein.

From such wells, further cloning is performed by, for example, a limiting dilution method, and thereby, clones can be obtained. Selection and breeding of hybridomas are generally performed in a medium for animal cells (for example, RPMI1640) containing 10-20% bovine embryo serum to which HAT (hypoxanthine, aminopterin, and thymidine) is added. The clones obtained as described above are transplanted into the abdominal cavity of a SCID mouse to which pristine is preliminarily administered, and ascitic fluid containing the monoclonal antibody at high concentration is collected after 10-14 days to serve as a material for antibody purification. Also, the clones can be cultured and the culture can be a material for antibody purification.

For the purification of the monoclonal antibody, a previously known method may be used as the purification method of immunoglobulin, and the purification can be easily achieved, for example, by an ammonium sulfate fraction method, a PEG fraction method, an ethanol fraction method, utilization of an anion exchanger, affinity chromatography in which a Nato3 protein is used, or the like.

The purification of the polyclonal antibody from the serum can be performed similarly.

[Detection Method]

The expression of a Nato3 gene serves as an index of the existence of dopaminergic neuron proliferative progenitor cells. Therefore, according to the present invention, by detecting expression of a Nato3 gene, the dopaminergic neuron proliferative progenitor cells can be detected or selected.

The method for "detecting expression of a Nato3 gene" used herein is not particularly limited as long as being capable of detecting the expression of a Nato3 gene in the cell samples to be tested, and, for example, includes hybridization methods, nucleic acid amplification methods, and antigen-antibody reaction methods.

The "cell samples to be tested" used herein can be cell samples that are thought to contain the dopaminergic neuron proliferative progenitor cells, and the cells in the midbrain ventral region can be used. The cells in the midbrain ventral region can be obtained by a known method (Studer, L., et al. Nature Neurosci (1998) 1:290-295). Preferably, fetus' (preferably, human aborted fetus') or the patient's own cells of the midbrain ventral region can be used as the cell samples to be tested. Moreover, the culture cells containing dopaminergic neuron proliferative progenitor cells induced to differentiate in vitro can be used as the cell samples to be tested. The induction to differentiate into the dopaminergic neuron proliferative progenitor cells in vitro can be performed by the differentiation treatment by a known method such as an SDIA method (Kawasaki et al. Neuron (2000) 28(1):31-40) or a 5-stage method (Lee, S H., et al. Nature Biotech (2000) 18:675-579) by using, as a starting material, known ES cells (Kawasaki et al. Neuron (2000) 28(1):31-40 and Lee, S H., et al. Nature Biotech (2000) 18:675-579), bone marrow stromal cells, immortalized cell line derived from nerve (Japanese Patent Laid-Open Publication No. 8-509215, No. 11-506930, and No. 2002-522070), neuron primordial cells (Japanese Patent Laid-Open Publication No. 11-509729), or the like. Preferably, ES cells subjected to the differentiation treatment by the SDIA method can be used as the cell samples to be tested.

The "SDIA method" used herein can be performed by co-culturing the ES cells and the stromal cell line PA6 in a serum-free medium (Kawasaki et al. Neuron (2000) 28(1): 31-40). Moreover, the "5-stage method" can be performed as follows. ES cells are cultured on a non-adherent culture plate under existence of the serum and thereby an embryoid body (EB) is formed, and sequentially, the EB is attached onto an adherent culture plate, and thereby, the neuron progenitor cells are selected. Finally, a growth factor such as Shh, FGF2, or FGF8 is added thereto, and thereby, dopaminergic neuron progenitor cells are induced (Lee, SH., et al. Nature Biotech (2000) 18:675-579).

According to the first embodiment of the detection method according to the present invention, the probe according to the present invention hybridizes with a nucleic acid sample (mRNA or transcript thereof), and the hybridization complex, namely, nucleotide double strand, is detected. Thus, the expression of the Nato3 gene can be detected in the cell samples.

For the detailed procedure of the hybridization method, there can be referred to "Molecular Cloning, A Laboratory Manual 2$^{nd}$ ed." (Cold Spring Harbor Press (1989), particularly Sections 9.47-9.58, "Current Protocols in Molecular Biology" (John Wiley & Sons (1987-1997)), particularly, Sections 6.3 and 6.4, "DNA Cloning 1: Core Techniques, A Practical Approach 2$^{nd}$ ed." (Oxford University (1995), particularly, Section 2.10 for the conditions).

The detection of expression of the Nato3 gene by utilizing the hybridization method can be performed, for example, by the following steps of:

(a) contacting a polynucleotide derived from a cell sample to be tested, with the polynucleotide probe according to the present invention; and
(b) detecting a hybridization complex.

In step (a), mRNA prepared from the cell sample to be tested that is thought to contain dopaminergic neuron proliferative progenitor cells or complementary DNA (cDNA) transcribed from the mRNA, as the polynucleotide derived from the cell sample to be tested, can be contacted with the probe.

In the detection method by using a probe, the probe can be labeled. The label includes a label by utilizing radioactivity (such as $^{32}$P, $^{14}$C, and $^{35}$S), fluorescence (such as FITC, europium), an enzyme (such as peroxidase or alkaline phosphatase) reaction such as chemical coloring, or the like.

The detection of the hybridization product can be performed by using a well-known method such as northern hybridization, southern hybridization, or colony hybridization.

The cells in which the hybridization complex is detected are those expressing a Nato3 gene, and therefore can be determined as the dopaminergic neuron proliferative progenitor cells.

According to the second embodiment of the detection method according to the present invention, the expression of the Nato3 gene can be detected in the cell sample by amplifying nucleic acid samples (mRNA or transcript thereof) by a nucleic acid amplification method using the primer or primer set according to the present invention, and detecting the amplification product is detected.

The detection of expression of the Nato3 gene by utilizing the nucleic acid amplification method can be performed, for example, by the following steps of:

(c) performing a nucleic acid amplification method by using a polynucleotide derived from a cell sample to be tested as a template and the polynucleotide primer or the polynucleotide primer set according to the present invention; and
(d) detecting a formed amplification product.

In step (c), mRNA prepared from the cell sample to be tested that is thought to contain dopaminergic neuron proliferative progenitor cells or complementary DNA (cDNA) transcribed from the mRNA can be used as the template.

The detection of the amplification product can be performed by using a nucleic acid amplification method such as a PCR method, a RT-PCR method, a real-time PCR method, or a LAMP method.

The cells in which the amplification product is detected are also expressing a Nato3 gene, and therefore can be determined as the dopaminergic neuron proliferative progenitor cells.

According to the third embodiment of the detection method according to the present invention, the antibody according to the present invention and the cell sample are contacted, and the antigen-antibody reaction is detected. Thus, the expression of a Nato3 gene can be detected in the cell sample.

The detection of expression of the Nato3 gene by utilizing the antigen-antibody reaction can be performed, for example, by the following steps of:

(e) contacting a protein derived from a cell sample to be tested, with the antibody according to the present invention; and
(f) measuring an antigen-antibody complex.

The method for detecting the antigen-antibody reaction is well-known for the skilled person, and, for example, a Nato3 protein can be detected in the cell sample to be tested that is thought to contain dopaminergic neuron proliferative progenitor cells by an immunological method. For the immunological method, a previously known method such as a immunohistologic staining method, an enzyme-linked immunosorbent assay, a western blotting method, an agglutination method, a competition method, or a sandwich method, can be applied to the cell sample subjected to appropriate treatment according to need, such as segregation or extraction operation of the cells. The immunohistologic staining method can be performed by, for example, a direct method by using a labeled antibody or an indirect method by using an labeled antibody against the antibody. For the labeling agent, a known labeling substance such as a fluorescent substance, a radioactive substance, an enzyme, a metal, or a pigment can be used.

The cells in which the antigen-antibody complex is detected are those expressing a Nato3 gene, and therefore can be determined as the dopaminergic neuron proliferative progenitor cells.

For use in the treatment of the Parkinson's disease, it is desirable that the purity of the dopaminergic neuron proliferative progenitor cells is high.

The accuracy of the detection or selection of the dopaminergic neuron proliferative progenitor cells can be enhanced by performing each of the above-described detection steps not only once but repeatedly.

Therefore, according to the detection method according to the present invention, the dopaminergic neuron proliferative progenitor cells can be detected or selected with high accuracy by performing the above-described step twice or more.

Moreover, the accuracy of detection or selection of the dopaminergic neuron proliferative progenitor cells can be enhanced by using together other marker genes, preferably dopaminergic neuron proliferative progenitor cell marker genes except for the Nato3 genes.

Therefore, according to the detection method according to the present invention, the dopaminergic neuron proliferative progenitor cells can be detected or selected with higher accuracy by using together dopaminergic neuron proliferative progenitor cell marker genes except for the Nato3 genes, postmitotic dopaminergic neuron precursor cell marker genes or the like, and detecting not only expression of the Nato3 gene but also expression of the other above-described marker genes The dopaminergic neuron-related marker genes expressing selectively in each of the differentiation stages are shown in FIG. 1.

In the detection method characterized in that the expression of the Nato3 gene is detected, the dopaminergic neuron proliferative progenitor cells can be detected or selected with high accuracy by detecting not only the Nato3 gene but also the dopaminergic neuron proliferative progenitor cell marker gene except for the Nato3 genes by using together dopaminergic neuron proliferative progenitor cell marker gene except for the Nato3 genes.

Specifically, in step (a), step (c), or step (e), the dopaminergic neuron proliferative progenitor cells can be detected or selected with high accuracy by using the cells in which the expression of the dopaminergic neuron proliferative progenitor cell marker gene except for the Nato3 genes is detected as the cell sample to be tested. In this case, the cells in which the hybridization complex is detected in the step (b), the cells in which the amplification product is detected in the step (d), and the cells in which the antigen-antibody complex is detected in the step (f) each express a Nato3 gene, and the dopaminergic neuron proliferative progenitor cell marker gene except for the Nato3 genes. Thus, the cells can be determined as the detected or selected dopaminergic neuron proliferative progenitor cells with high accuracy.

Moreover, the dopaminergic neuron proliferative progenitor cells can be detected or selected with high accuracy by performing step (g-1) of detecting expression of the dopaminergic neuron proliferative progenitor cell marker gene except for the Nato3 genes with respect to the cells in which the hybridization complex is detected in step (b), the cells in which the amplification product is detected in step (d), and the cells in which the antigen-antibody complex is detected in step (f), respectively. In this case, in step (g-1), the cells in which the expression of the dopaminergic neuron proliferative progenitor cell marker gene except for the Nato3 genes is detected are those expressing a Nato3 gene, and the dopaminergic neuron proliferative progenitor cell marker gene except for the Nato3 genes. Thus, the cells can be determined as the detected or selected dopaminergic neuron proliferative progenitor cells with high accuracy.

In the detection method characterized in that the expression of the Nato3 gene is detected, by using together a postmitotic dopaminergic neuron precursor cell marker gene, it can be confirmed that the Nato3 gene is expressed but the expression of the postmitotic dopaminergic neuron precursor cell marker gene is not detected. Thus, the dopaminergic neuron proliferative precursor cells can be detected or selected with high accuracy.

Specifically, in step (a), step (c), or step (e), the dopaminergic neuron proliferative progenitor cells can be detected or selected with high accuracy by using the cells in which the expression of the postmitotic dopaminergic neuron precursor cell marker gene is not detected. In this case, the cells in which the hybridization complex is detected in step (b), the cells in which the amplification product is detected in step (d), and the cells in which the antigen-antibody complex is detected in step (f) each express a Nato3 gene but does not express the postmitotic dopaminergic neuron precursor cell marker gene. Thus, the cells can be determined as the detected or selected dopaminergic neuron proliferative progenitor cells with high accuracy.

Moreover, the dopaminergic neuron proliferative progenitor cells can be detected with high accuracy by performing step (g-2) of detecting expression of the postmitotic dopaminergic neuron precursor cell marker gene with respect to the cells in which the hybridization complex is detected in step (b), the cells in which the amplification product is detected in step (d), and the cells in which the antigen-antibody complex is detected in step (f), respectively. In this case, in step (g-2), the cells in which the expression of the postmitotic dopaminergic neuron precursor cell marker gene is not detected are those expressing a Nato3 gene, but not the postmitotic dopaminergic neuron precursor cell marker gene. Thus, the cells can be determined as the detected or selected dopaminergic neuron proliferative progenitor cells with high accuracy.

"The dopaminergic neuron proliferative progenitor cell marker gene except for the Nato3 genes" includes a dopaminergic neuron proliferative progenitor cell marker gene except for a Nato3 gene which is expressed in the midbrain's most ventral ventricular region (VZ region), and includes an Lrp4 gene, an Msx1 gene, an Msx2 gene, and a Mash1 gene.

An Lrp4 gene is described in WO 2004/065599. A Mash1 gene is described in Kele J, Simplicio N, Ferri A L, Mira H, Guillemot F, Arenas E, Ang S L. Neurogenin 2 is required for the development of ventral midbrain dopaminergic neurons, and Development. 2006 February; 133(3):495-505. It has been confirmed by the present inventors that an Msx1 gene and an Msx2 gene are expressed selectively in the dopaminergic neuron proliferative progenitor cells (the data not shown).

The detection of the dopaminergic neuron proliferative progenitor cell marker gene except for the Nato3 genes is not limited as long as using a method by which expression of the known gene can be detected, and, for example, includes the above-described hybridization method, the nucleic acid amplification method, and the antigen-antibody reaction method.

"The postmitotic dopaminergic neuron precursor cell marker gene" includes a gene expressed in the midbrain's most ventral mantle layer (ML region), and includes a Nurr1 gene, an En1 gene, an En2 gene, a Ptx3 gene, and a TH gene. Moreover, the marker gene includes a gene expressed in the midbrain's most ventral ventricular region (VZ region), and includes a 65B13 gene.

A Nurr1 gene is described in Science. 1997 11; 276(5310): 248-50. An En1 gene is described in J. Neurosci. 2001 21(9): 3126-34. An En2 gene is described in J. Neurosci. 2001 21(9) 3126-34. A Ptx3 gene is described in Proc. Natl. Acad. Sci. 1997 94: 13305-10. A TH gene is described in Science 1997 11; 276(5310):248-50. A 65B13 gene is described in WO 2004/038018.

The detection of the postmitotic dopaminergic neuron precursor cell marker gene is not particularly limited as long as using a method by which expression of the known gene can be detected, and, for example, includes the above-described hybridization method, the nucleic acid amplification method, and the antigen-antibody reaction method.

[Detection Kit]

The present invention provides a detection kit for performing the detection method according to the present invention.

The first embodiment of the detection kit according to the present invention includes a detection kit for performing the detection method of the first embodiment according to the present invention, and specifically, a kit for detecting the expression of the Nato3 gene, including at least the probe according to the present invention. The probe may be labeled. The detection kit detects the expression of the Nato3 gene by a hybrid formation method.

Therefore, the detection method of the first embodiment can optionally further include various reagents for performing the hybrid formation method such as a substrate compound used for detection of the marker, hybridization buffer, instructions, equipment, and/or so forth.

For performing the detection with high accuracy, the detection kit of the first embodiment according to the present invention may further include the probe, the primer, the primer set, or the antibody which can detect the expression of the dopaminergic neuron proliferative progenitor cell marker gene except for the Nato3 genes, or the expression of the postmitotic dopaminergic neuron precursor cell marker gene. The probe, the primer, the primer set, or the antibody may be labeled. By any of the hybrid formation method, the nucleic acid amplification method, and the antigen-antibody reaction method, the detection kit further detects the expression of the dopaminergic neuron proliferative progenitor cell marker gene except for the Nato3 genes, or the expression of the postmitotic dopaminergic neuron precursor cell marker gene.

The second embodiment of the detection kit according to the present invention includes a detection kit for performing the detection method of the second embodiment according to the present invention, and specifically, a kit for detecting the expression of the Nato3 gene, including at least the primer according to the present invention or the primer set according to the present invention. The detection kit detects the expression of the Nato3 gene by the nucleic acid amplification method.

Therefore, the detection method of the second embodiment can optionally further include various reagents for performing the nucleic acid amplification method such as a buffer, an internal standard indicating that the PCR can normally progress, instructions, equipment, and/or so forth.

For performing the detection with high accuracy, the detection kit of the second embodiment according to the present invention may further include the probe, the primer, the primer set, or the antibody which can detect the expression of the dopaminergic neuron proliferative progenitor cell marker gene except for the Nato3 genes, or the expression of the postmitotic dopaminergic neuron precursor cell marker gene. The probe, the primer, the primer set, or the antibody may be labeled. By any of the hybrid formation method, the nucleic acid amplification method, and the antigen-antibody reaction method, the detection kit further detects the expression of the dopaminergic neuron proliferative progenitor cell marker gene except for the Nato3 genes, or the expression of the postmitotic dopaminergic neuron precursor cell marker gene.

The third embodiment of the detection kit according to the present invention includes a detection kit for performing the detection method of the third embodiment according to the present invention, and specifically, a kit for detecting the expression of the Nato3 gene, including at least the antibody according to the present invention. The antibody may be labeled. The detection kit detects the expression of the Nato3 gene by detecting the antigen-antibody reaction.

Therefore, the detection method of the third embodiment can optionally further include various reagents for performing the antigen-antibody reaction such as a secondary antibody used for the ELISA method or the like, a coloring reagent, a buffer, instructions, equipment, and/or so forth.

For performing the detection with high accuracy, the detection kit of the third embodiment according to the present invention may further include the probe, the primer, the primer set, or the antibody which can detect the expression of the dopaminergic neuron proliferative progenitor cell marker gene except for the Nato3 genes, or the expression of the postmitotic dopaminergic neuron precursor cell marker gene. The probe, the primer, the primer set, or the antibody may be labeled. By any of the hybrid formation method, the nucleic acid amplification method, and the antigen-antibody reaction method, the detection kit further detects the expression of the dopaminergic neuron proliferative progenitor cell marker gene except for the Nato3 genes, or the expression of the postmitotic dopaminergic neuron precursor cell marker gene.

[Screening Method]

The detection method according to the present invention can be applied to screening for effective substances for inducing differentiation into the dopaminergic neuron proliferative progenitor cells. Specifically, effective substances for inducing differentiation into dopaminergic neuron proliferative progenitor cells can be screened for by determining whether or not the addition of a substance to be tested has induced the differentiation into the dopaminergic neuron proliferative progenitor cells using expression of a Nato3 gene as an index.

Therefore, the present invention provides a method for screening for an effective substance for inducing differentiation into a dopaminergic neuron proliferative progenitor cell, comprising the following steps of:

(i) contacting a cell that can differentiate into a dopaminergic neuron proliferative progenitor cell, with a substance to be tested; and (ii) detecting expression of a Nato3 gene in the cell contacted with the substance to be tested.

The cell that can differentiate into a dopaminergic neuron proliferative progenitor cell in step (i) can be preferably collected from an embryonic midbrain ventral region or from culture cells containing neuron progenitor cells induced to differentiate from ES cells.

"Contacting with a substance to be tested" in step (i) can be performed by, for example, adding the substance to be tested to culture cells containing the cells that can differentiate into a dopaminergic neuron proliferative progenitor cell.

"Substance to be tested" includes a synthesized low-molecular compound, a protein, a synthesized peptide, a purified or partially purified polypeptide, an antibody, a bacterium-releasing material (comprising bacterial metabolite), and a nucleic acid (such as antisense, ribozyme, and RNAi), and is preferably a synthesized low-molecular compound, but is not limited thereto. "Substance to be tested" may be a novel substance or a known substance.

In step (ii), according to the detection method of the present invention, the expression of the Nato3 gene can be detected.

Specifically, steps (a) and (b) are performed for the detection by utilizing the hybridization method. Steps (c) and (d) are performed for the detection by utilizing the nucleic acid amplification method. Steps (e) and (f) are performed for the detection by utilizing the antigen-antibody reaction. Thus, the expression of the Nato3 gene can be detected.

In step (ii), when the expression of the Nato3 gene is detected in the cell sample by contacting the substance to be tested, the substance can be determined as the effective substance for inducing differentiation into the dopaminergic neuron proliferative progenitor cells.

The substance specified by the screening method according to the present invention can be used as the effective substance for inducing differentiation into the dopaminergic neuron proliferative progenitor cells.

The present invention provides the method for screening for an effective substance for inducing differentiation into a dopaminergic neuron proliferative progenitor cell, further comprising the step of:
(iii) detecting expression of the dopaminergic neuron proliferative progenitor cell marker gene except for the Nato3 genes.

When the expression of the Nato3 gene is detected in step (ii) and the expression of the dopaminergic neuron proliferative progenitor cell marker gene except for the Nato3 genes is detected in step (iii), the substance can be determined as the effective substance for inducing differentiation into dopaminergic neuron proliferative progenitor cells, with high accuracy.

Step (iii) may be performed after step (i) and may be performed before or after the step (ii).

"The dopaminergic neuron proliferative progenitor cell marker gene except for the Nato3 genes" includes the dopaminergic neuron proliferative progenitor cell marker gene except for the Nato3 genes that are expressed in the midbrain most ventral ventricular region (VZ region), and, for example, includes an Lrp4 gene, an Msx1 gene, an Msx2 gene, and a Mash1 gene.

The detection of the dopaminergic neuron proliferative progenitor cell marker gene except for the Nato3 genes is not particularly limited as long as using a method by which the expression of the known gene can be detected, for example, includes the above-described hybridization method, the nucleic acid amplification method, and the antigen-antibody reaction method.

[Production Method]

The detection method according to the present invention can detect or select the dopaminergic neuron proliferative progenitor cells. The dopaminergic neuron proliferative progenitor cells for use in the treatment of the Parkinson's disease. Therefore, the dopaminergic neuron proliferative progenitor cells for use in the treatment of the Parkinson's disease can be produced from the detected or selected dopaminergic neuron proliferative progenitor cells using the expression of a Nato3 gene as an index.

The present invention provides a method for producing a dopaminergic neuron proliferative progenitor cell, comprising the steps of:
(iv) obtaining cells that can contain a dopaminergic neuron proliferative progenitor cell;
(v) detecting or selecting the dopaminergic neuron proliferative progenitor cell by using the detection method according to the present invention; and
(vi) culturing the cell detected or selected in step (v).

The present invention provides a method for treating the Parkinson's disease comprising the step of transplanting the dopaminergic neuron proliferative progenitor cells detected or selected by the detection method according to the present invention, or the dopaminergic neuron proliferative progenitor cells produced by the production method according to the present invention, into a mammal including a human.

According to the treatment method of the present invention, the transplanted dopaminergic neuron proliferative progenitor cells produce dopamine, and thus, the Parkinson's disease can be prevented and/or treated.

When the treatment method according to the present invention is performed, the cells that can contain the dopaminergic neuron proliferative progenitor cells can be collected from a mammal comprising a human, and preferably, the individual subjected to the transplantation or an aborted fetus.

The dopaminergic neuron proliferative progenitor cells can be transplanted into a brain, preferably, a midbrain.

In the present specification, "detection" includes "discrimination".

EXAMPLES

Hereinafter, the present invention will be specifically explained by Examples, but the following Examples do not limit the scope of the present invention.

Example 1

Expression Analysis of Nato3 Gene (1) Analysis by RT-PCR Method

In order to confirm that a Nato3 gene is expressed in the cells of dopaminergic neuron lineage, expressions of mRNAs of Nato3, DAT, Lmx1a, and Lrp4 in each region of a mouse embryonic midbrain were investigated by a RT-PCR method according to the following protocol. Here, DAT is a marker gene of the dopaminergic neuron (Development. 2004; 131 (5):1145-55.), Lmx1a is a marker gene of dopaminergic neurons and dopaminergic neuron progenitor cells (WO2005/052190), and Lrp4 is a marker gene of the dopaminergic neuron proliferative progenitor cells (WO2004/065599).

Figure 2:
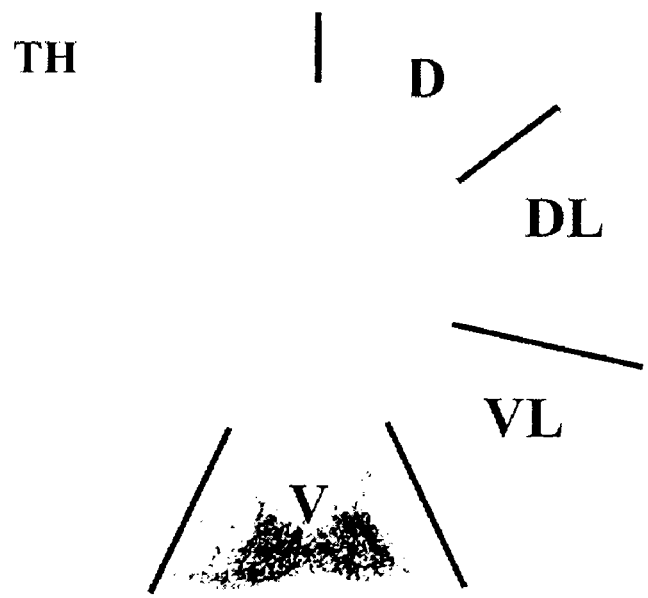
FIG. 2 shows a midbrain of a 12.5-day mouse embryo. The midbrain is divided into four regions along the dorsoventral axis (V: most ventral region, VL: ventral lateral region, DL: dorsal lateral region, D: most dorsal region)

From a 12.5-day mouse (obtained from SLC) embryo, 4 regions (V region: most ventral region, VL region: ventral lateral region, DL region: dorsal lateral region, and D region: most dorsal region) of the midbrain shown in FIG. 2 were cut out, and the total RNA was prepared by using a RNeasy mini kit (Qiagen), and double-strand cDNA was synthesized by using a cDNA synthesis kit (TAKARA). Next, the synthesized cDNA was digested with the restriction enzyme RsaI (TAKARA), and then, ad2 was added thereto, and PCR was performed at 15 cycles using ad2S as a primer, and thereby, cDNA was amplified and used as a template for RT-PCR. The amplification was carried out under the conditions that incubation was performed for 5 minutes at 72° C., and then reactions for 30 seconds at 94° C., for 30 seconds at 65° C., and for 2 minutes at 72° C., were performed at 15 cycles, and finally, incubation was performed for 2 minutes at 72° C.

```
ad2S:
cagctccacaacctacatcattccgt    (SEQ ID NO: 21)

ad2A:
acggaatgatgt                  (SEQ ID NO: 22)
```

Next, by using the cDNAs corresponding to the amplified cDNA of 4 ng, 0.4 ng, and 0.04 ng as templates, PCR was performed in the following reaction system.

| | |
|---|---|
| 10xExTaq | 1 μl |
| 2.5 mM dNTP | 0.8 μl |
| ExTaq | 0.05 μl |
| 100 μM primer | 0.1 μl for each |
| cDNA | 1 μl |
| Distilled water | 6.95 μl |

After incubation for 2 minutes at 94° C., the amplification reaction for 30 seconds at 94° C., for 30 seconds at 65° C., and for 2 minutes at 72° C., was performed, and finally, incubation was performed for 2 minutes at 72° C. The PCR amplifications were performed at 26 cycles for Lrp4, DAT and Lmx1a, and at 25 cycles for Nato3.

The following primers were used in the PCR.

```
Lrp4:
tagtctaccactgctcgactgtaacg    (SEQ ID NO: 23)

cagagtgaacccagtggacatatctg    (SEQ ID NO: 24)

DAT:
cagaatcctgtgctcacggtagttgc    (SEQ ID NO: 25)

actaaagtggctgcaagctgaccagg    (SEQ ID NO: 26)

Lmx1a:
tggttcaggtgtggttccagaaccag    (SEQ ID NO: 27)

tctgaggttgccaggaagcagtctcc    (SEQ ID NO: 28)

Nato3:
cctgggaagactgtcgcagtttgatg    (SEQ ID NO: 29)

gaaggcctcgtttaggttgaacatcc    (SEQ ID NO: 30)
```

Figure 3:
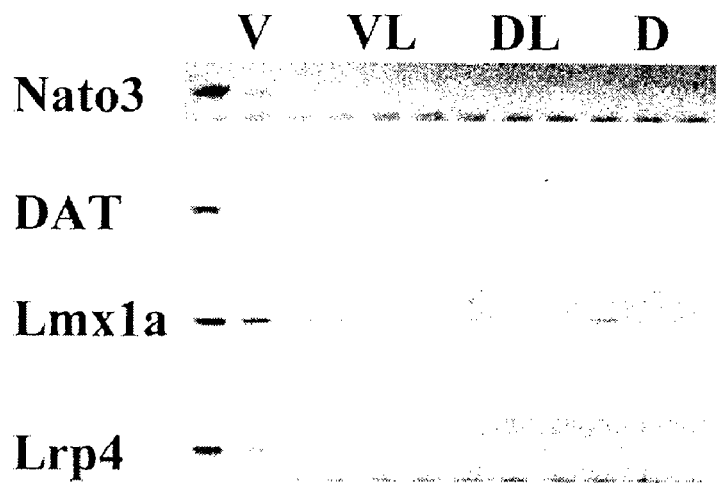
FIG. 3 shows the results of analyzing, by the RT-PCR method, mRNA expression of Nato3, DAT, Lmx1a and Lrp4 in each of the regions of the midbrain.

As a result, it became revealed that mRNA of Nato3 is selectively expressed in the V region of the midbrain in which the marker genes of dopaminergic neuron and dopaminergic neuron progenitor cells are expressed (FIG. 3).

(2) Analysis by in situ Hybridization

Furthermore, in order to investigate the expression pattern in detail, by in situ hybridization according to the following protocol, expression analysis of mRNA of Nato3, Nurr1, and tyrosine hydroxylase (TH) was performed. Nurr1 and TH are marker genes that are known to be induced to express first after postmitotic in the dopaminergic neuron precursor cells (Science. 1997 11; 276(5310): 248-50.).

First, a DIG-probe was produced by the following method.

From a 12.5-day mouse (obtained from SLC) embryo, the midbrain afterbrain region was cut out, and the total RNA was prepared by using the RNeasy mini kit (Qiagen), and double-strand cDNA was synthesized by using the cDNA synthesis kit (TAKARA). By using the synthesized cDNA as a template, cDNAs of Nato3, Nurr1, and TH were amplified in the following reaction system.

| | |
|---|---|
| 10xExTaq | 5 μl |
| 2.5 mM dNTP | 4 μl |
| ExTaq | 0.25 μl |
| 100 μM primer | 0.5 μl for each |
| cDNA | 1 μl |
| Distilled water | 38.75 μl |

The amplification was carried out under the conditions that incubation was performed for 5 minutes at 94° C., and then reactions for 30 seconds at 94° C., for 30 seconds at 65° C., and for 2 minutes at 72° C., were performed at 35 cycles, and finally, incubation was performed for 2 minutes at 72° C.

The following primers were used in the PCR.

```
Nato3:
atcggcagctatgccattcctgcaag    (SEQ ID NO: 31)

tgctccaagcaagaagctctaactcc    (SEQ ID NO: 32)

TH:
gctgtcacgtccccaaggttcattgg    (SEQ ID NO: 33)

ggagcgcatgcagtagtaagatgtgg    (SEQ ID NO: 34)

Nurr1:
catatgatcgagcagaggaagacacc    (SEQ ID NO: 35)

agtgcgaacaccgtagtgctgacagg    (SEQ ID NO: 36)
```

The amplified cDNA fragments were cloned into pCRII (Invitrogen) and used as templates, and thereby, DIG-probes were synthesized by the following reaction system (all of the reagents were purchased from Roche)

| | |
|---|---|
| RNA Polymerase Buffer | 2 μl |
| NTP Labeling Mix | 2 μl |
| RNase Inhibitor | 1 μl |
| RNA polymerase (T7 or SP6) | 2 μl |
| Template DNA | 1 μg |
| Distilled water | Total 20 μl |

After 2 hours at 37° C., DNaseI (Roche) treatment was performed for 15 minutes at 37° C., and the DIG-RNA probe was collected by ethanol precipitation.

Next, an 11.5-day mouse embryo was excised and fixed for 2 hours at 4° C. by using 4% PFA (WAKO)/PBS (−), and then, the solution was replaced at 4° C. overnight by 20% sucrose (WAKO)/PBS (−) and then the embryo was embedded with OCT (Sakura Seiki Co., Ltd.). Sections of 12 μm thickness were prepared and dried on slide glasses and then fixed again for 30 minutes at room temperature by using 4% PFA. After rinsing with PBS, hybridization (1 μg/ml DIG-RNA probe, 50% formamide (Nacalai Tesque, Inc.), 5×SSC, 1% SDS, 50 μg/ml yeast RNA (Sigma), 50 μg/ml heparin) was performed for 40 hours at 68° C. Then, rinsing (50% formamide, 5×SSC, and 1% SDS) was performed at 68° C. and further rinsing (50% formamide, 5×SSC) was performed at 68° C. After rinsing with 1×TBST at room temperature, blocking (blocking agent: Roche) was performed. Alkaline phosphatase-labeled anti-DIG antibody (DAKO) was reacted at 4° C. overnight, and after rinsing (1×TBST, 2 mM levamisole), NBT/BCIP (DAKO) was used as the substrate for coloring.

Figure 4:
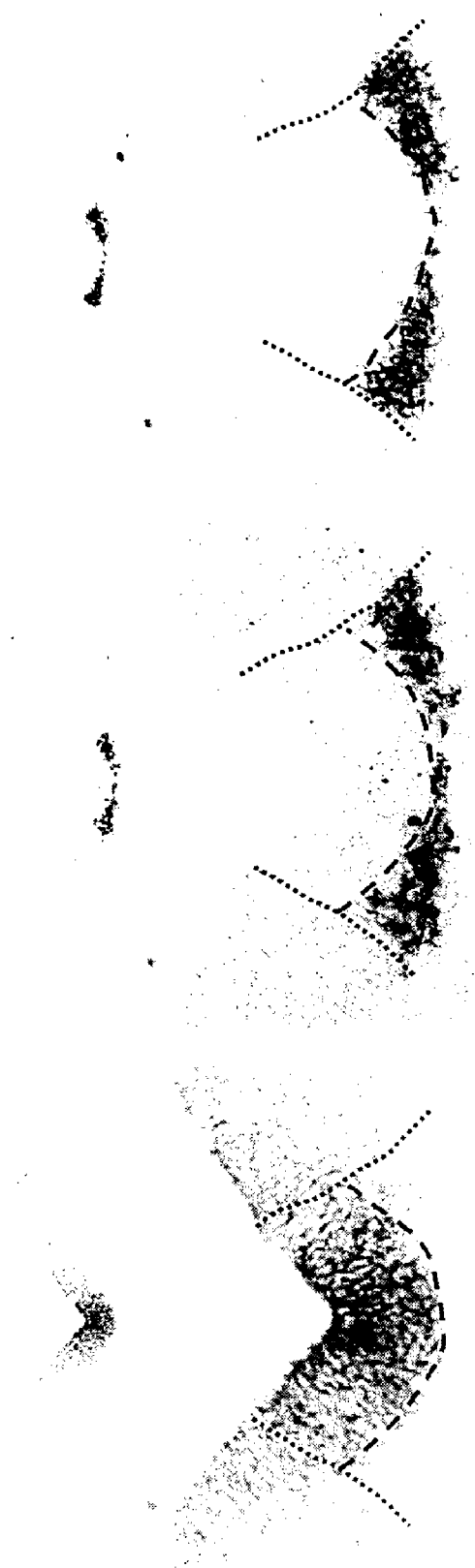
FIG. 4 shows the results of analyzing, by in situ hybridization, mRNA expression of Nato3, Nurr1, and TH in the midbrain of an 11.5-day mouse embryo. Dotted lines represent a region in which dopaminergic neurons are generated, and dash lines represent borders between VZ (ventricular zone) and ML (mantle layer).

As a result, in the 11.5-day mouse embryo which is in the period of generating dopaminergic neurons, it became revealed that mRNA of Nato3 is strongly expressed in the V region in the same manner as TH and Nurr1 (FIG. 4). Also, by contrast that mRNA of TH and Nurr1 is expressed only in the mantle layer (ML) region in which the postmitotic neurons exist, it became revealed that mRNA of Nato3 is not expressed in the ML region but is expressed only in the ventricular zone (VZ) in which the proliferative progenitor cells exist (FIG. 4). From the above-described results, it became revealed that mRNA of Nato3 is selectively and strongly expressed in the dopaminergic neuron proliferative progenitor cells.

Example 2

Expression Analysis of Nato3 Protein

Next, by using anti-Nato3 antibody, the expression of Nato3 protein was studied. Moreover, double staining by using an anti-Lmx1a antibody and an anti-Nurr1 antibody was performed.

First, the 1-92 amino acid region of Nato3 protein was expressed as a fusion protein with a GST protein in *E. Coli* JM109 cell line (TAKARA) and collected. A rat was immunized with the collected fusion protein, and then, a lymphocyte cell was taken out and cell-fused to a myeloma P3U1, and thereby, an anti-Nato3 antibody-producing hybridoma was obtained (hybridoma production was outsourced to Kojin-Bio Co., Ltd.). Similarly, the 271-307 amino acid region of the Lmx1a protein was expressed as a fusion protein with the GST protein and collected. A hamster (obtained from SLC) was immunized with the collected fusion protein, and then, the lymphocyte cells were taken out and cell-fused to a myeloma (ATCC), and thereby, an anti-Lmx1a antibody-producing hybridoma was obtained.

A 11.5-day mouse embryo was excised and fixed for 2 hours at 4° C. by using 4% PFA (WAKO)/PBS (−), and then, the solution was replaced at 4° C. overnight by 20% sucrose (WAKO)/PBS (−) and then the embryo was embedded with OCT (Sakura Seiki Co., Ltd.). Sections of 12 μm thickness were prepared, mounted on slide glasses, dried for 30 minutes at room temperature, and then moistened again with PBS (−). Next, blocking (Blockase (Dainippon Sumitomo Pharma Co., Ltd.)) was performed for 30 minutes at room temperature, and then, reaction with a primary antibody (anti-Nato3 and anti-Lmx1a antibodies from above-described hybridoma culture supernatant, anti-Nurr1 antibody from Santa Cruz) was performed for one hour at room temperature, and then, reaction was further performed at 4° C. overnight. By using 0.1% Tween-20/PBS (−), rinsing was performed for 15 minutes at room temperature three times. Next, a fluorescence-labeled secondary antibody (Jackson) was reacted for one hour at room temperature and rinsing was performed in the same manner, and then, rinsing with PBS(−) was performed for 10 minutes at room temperature, and sealed.

Figure 5:
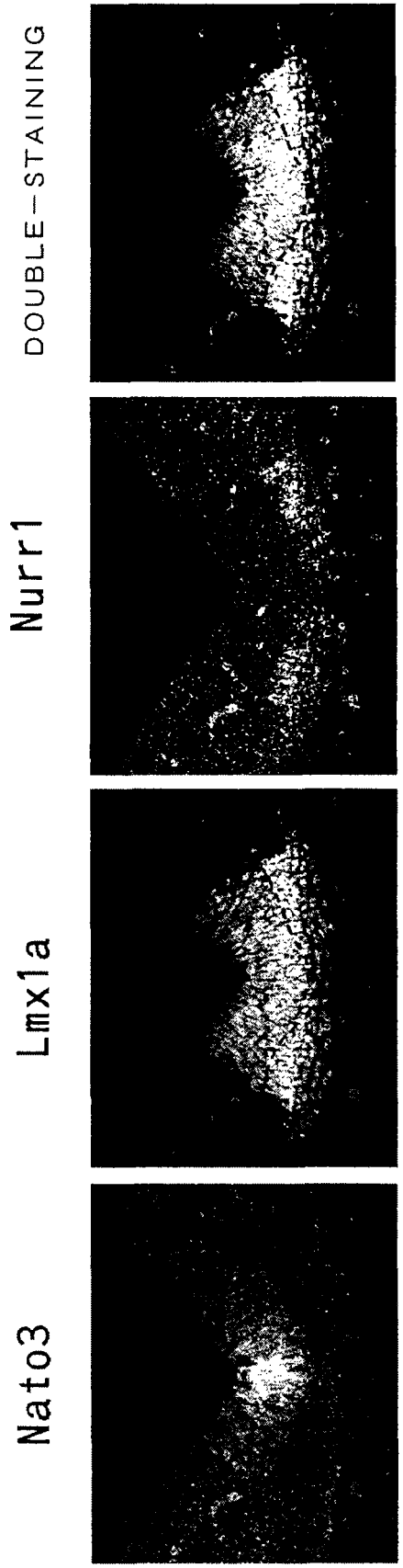
FIG. 5 shows the results of analyzing, by an immunostaining method, protein expression of Nato3, Lmx1a and Nurr1, and coexpression thereof (double staining) in the midbrain of an 11.5-day mouse embryo. Dotted lines represent a region in which dopaminergic neurons are generated, and dash lines represent borders between VZ (ventricular zone) and ML (mantle layer)

As a result, it became revealed that Nato3 is expressed in the midbrain of the 11.5-day mouse embryo as protein as well as mRNA (FIG. 5). From the result of double staining with anti-Lmx1a antibody and anti-Nurr1 antibody, it was confirmed that Nato3 protein is co-expressed with the Lmx1a protein, and thus it became revealed that the Nato3 protein is expressed selectively in the dopaminergic neuron proliferative progenitor cells (FIG. 5). Moreover, it was confirmed that the Nato3 protein is expressed selectively in the VZ region in which a Nurr1 protein is not expressed, and thus it became revealed that the Nato3 protein is expressed selectively in the dopaminergic neuron proliferative progenitor cells (FIG. 5).

Example 3

Expressions of Nato3 Gene in Dopaminergic Neurons Induced to Differentiate from ES Cells Whether a Nato3 gene is expressed when ES cells are induced to differentiate into dopaminergic neurons was studied.

First, according to the SDIA method (Kawasaki et al. Neuron. 2000 28(1):31-40.), ES cells (mouse CCE strain provided from Mr. Nishikawa in Riken CDB, Kawasaki et al. Neuron. 2000 28(1):31-40.) was induced to differentiate into dopaminergic neurons. The cells were collected after 4, 6, 8, 10, 12 days after the induction. The total RNA was prepared by using the RNeasy mini kit (Qiagen), and RT-PCR was performed. First, with respect to 1 μg of the total RNA, cDNA synthesis was performed by using the RNA PCR kit (TAKARA). By using the cDNAs corresponding to 10 ng, 1 ng, and 0.1 ng as templates, PCR was performed in the following reaction system.

| | |
|---|---|
| 10×ExTaq | 2 μl |
| 2.5 mM dNTP | 1.6 μl |
| ExTaq | 0.1 μl |
| 100 μM primer | 0.2 μl for each |
| cDNA | 1 μl |
| Distilled water | 14.9 μl |

After incubation for 2 minutes at 94° C., the reaction for 30 seconds at 94° C., for 30 seconds at 65° C., and for 2 minutes at 72° C., was performed at 35 cycles, and finally, incubation was performed for 2 minutes at 72° C.

The following primers were used in the PCR.

```
TH:
gttcccaaggaaagtgtcagagttgg     (SEQ ID NO: 37)

gaagctggaaagcctccaggtgttcc     (SEQ ID NO: 38)

DAT:
ctccgagcagacaccatgacttagc      (SEQ ID NO: 39)

aggagtagggcttgtctcccaacctg     (SEQ ID NO: 40)

Nurr1:
cactcctgtgtctagctgccagatgc     (SEQ ID NO: 41)

agtgcgaacaccgtagtgctgacagg     (SEQ ID NO: 42)

Ptx3:
tgagccgcaggtctgtggatccatcc     (SEQ ID NO: 43)

tccctgttcctggccttagtcctagg     (SEQ ID NO: 44)

En1:
atcctccgagtggacattcacatagg     (SEQ ID NO: 45)

atgtccagcaaatagagatcgctacac    (SEQ ID NO: 46)
```

In addition, for Nato3 and Lmx1a, the primers of Example 1 were used. Moreover, Ptx3 and En1 are known as markers of the postmitotic dopaminergic neuron precursor cells.

Figure 6:
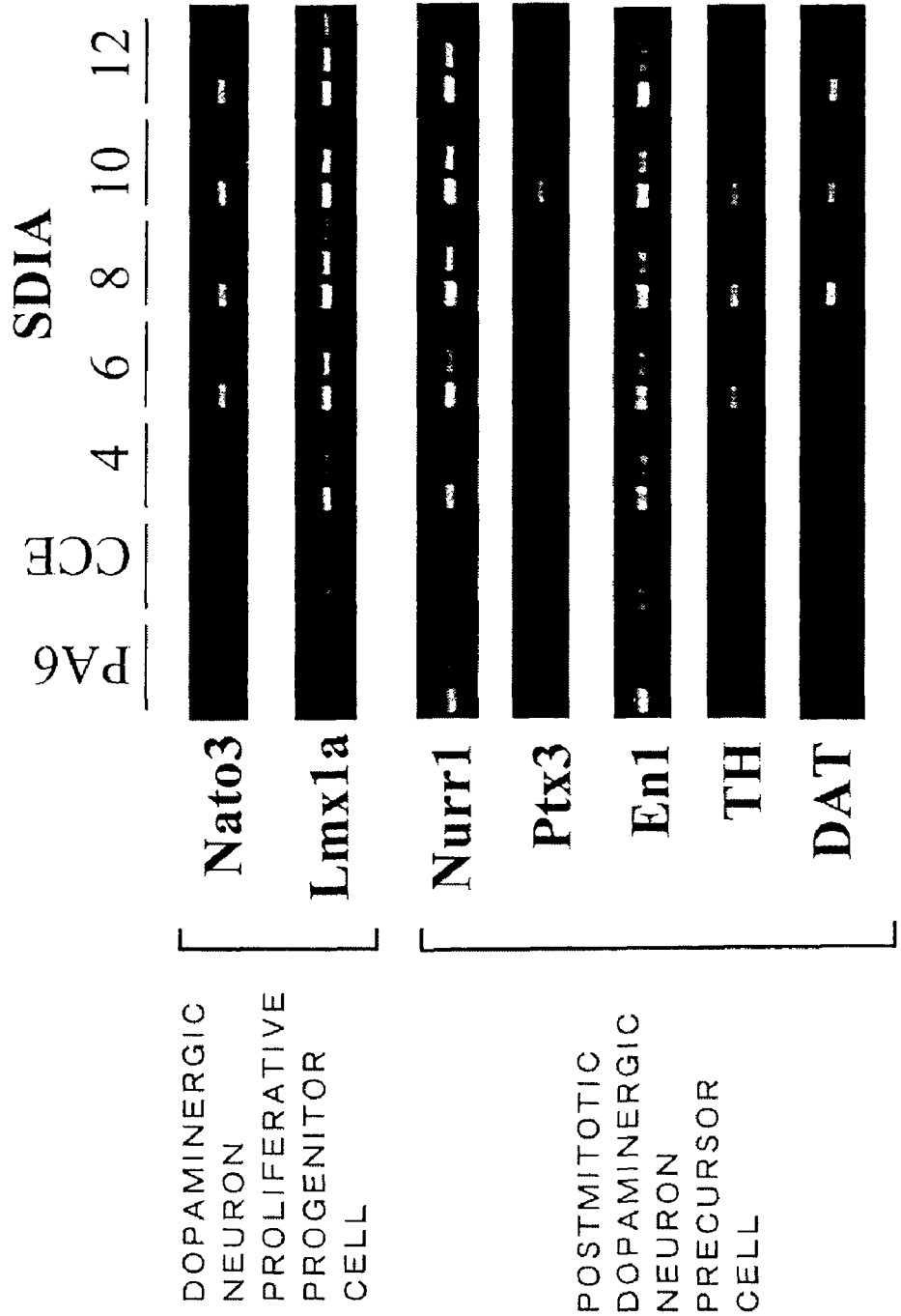
FIG. 6 shows the results of analyzing, by the RT-PCR method, expressions of Nato3 and other dopaminergic neuron marker genes in dopaminergic neuron progenitor cells induced to differentiate from ES cells.

As a result, expression of mRNA of Nato3 was not recognized in ES cells (CCE) and stromal cells (PA6), but it became revealed that as a result of the differentiation induction, the expression is induced from the fourth day in the same manner as Lmx1a, which is a marker gene of the dopaminergic neuron proliferative progenitor cells (FIG. 6).

Example 4

Expression of Nato3 Gene in Dopaminergic Neuron Proliferative Progenitor Cells Sorted by Lrp4

In order to confirm that a Nato3 gene is expressed in the dopaminergic neuron proliferative progenitor cells, the dopaminergic neuron proliferative progenitor cells were separated from the cells derived from the midbrain of a 12.5-day mouse embryo and SDIA differentiation induction cells respectively using a Lrp4 gene which is expressed selectively in the dopaminergic neuron proliferative progenitor cells as a marker, and the expression of mRNA of Nato3 in these cells was investigated.

First, a gene sequence encoding the extracellular region (161-502 amino acids) in an Lrp4 gene was gene-transfected into 293E cells (ATCC), and the extracellular region of the Lrp4 protein was expressed and collected. A hamster (obtained from SLC) was immunized with the collected protein, and then, lymphocytic cells were extracted and cell-fused with myeloma cells (ATCC) to obtain an anti-Lrp4 antibody-producing hybridoma.

Figure 7:
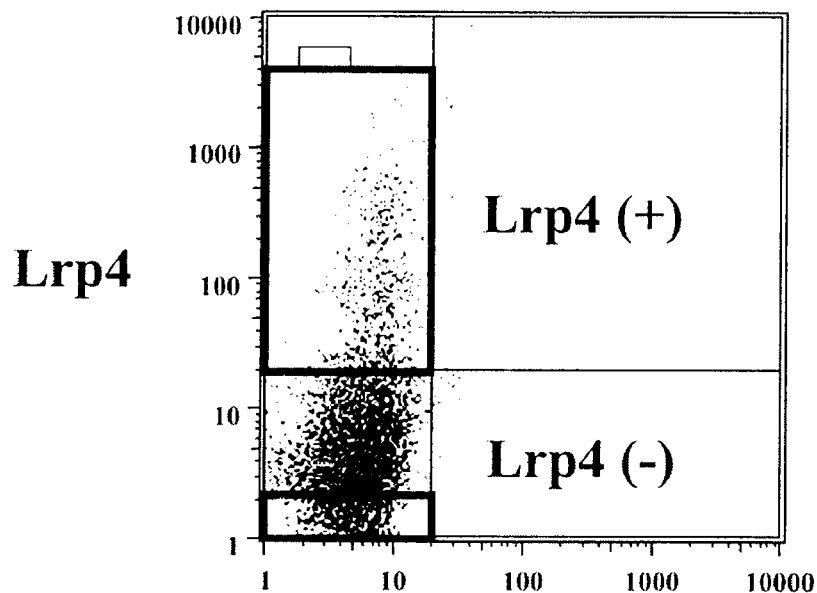
FIG. 7 shows separation of Lrp4 positive cells and negative cells by a cell sorter.

The group of the cells containing the dopaminergic neuron progenitor cells derived from the midbrain of the 12.5-day mouse embryo or induced to differentiate from ES cells in vitro was dispersed by using a cell dissociation Buffer™ (Invitrogen), and then, without being subjected to fixation and permeabilization treatments, the cells were stained for 20 minutes at 4° C. by using an anti-Lrp4 monoclonal antibody (a culture supernatant diluted to 1/2, 1% fetal bovine serum (JRH), 1 mM EDTA/SDIA differentiation medium (Kawasaki et al. Neuron (2000)28(1):31-40)). Then, with 1% fetal bovine serum and 1 mM EDTA/SDIA differentiation medium, rinsing was performed for 3 minutes at 4° C. three times, and the cells were stained for 20 minutes at 4° C. by using a biotin-labeled anti-hamster IgG antibody (Jackson, 10 μg/ml, 1% fetal bovine serum, 1 mM EDTA/SDIA differentiation medium), and then, rinsing was performed in the same manner. The cells were stained for 20 minutes at 4° C. by using a PE-labeled streptavidin (Pharmingen, 20 μg/ml, 1% fetal bovine serum, 1 mM EDTA/SDIA differentiation medium), and then, rinsing was performed in the same manner. After the staining, Lrp4 positive cells and negative cells were separated by a cell sorter (FACS vantage SE, Becton Dickinson) (FIG. 7). The total RNA was prepared from the cells immediately after the separation, by using the RNeasy mini kit (Qiagen), and the double stand cDNA was synthesized by using the cDNA synthesis kit (TAKARA). After digestion with restriction enzyme RsaI (TAKARA), ad2 was added thereto, and ad2S was used as a primer, and the cDNA was amplified by PCR of 15 cycles and used for the template for RT-PCR. The amplification was carried out under the conditions that incubation was performed for 5 minutes at 72° C., and then reactions for 30 seconds at 94° C., for 30 seconds at 65° C., and for 2 minutes at 72° C., were performed at 15 cycles, and finally, incubation was performed for 2 minutes at 72° C.

Next, by using the cDNAs corresponding to the amplified cDNA of 4 ng, 0.4 ng, and 0.04 ng as templates, PCR was performed in the following reaction system.

| | |
|---|---|
| 10xExTaq | 1 μl |
| 2.5 mM dNTP | 0.8 μl |
| ExTaq | 0.05 μl |
| 100 μM primer | 0.1 μl for each |
| cDNA | 1 μl |
| Distilled water | 6.95 μl |

The primers having the above-described sequences were used.

After incubation for 2 minutes at 94° C., the amplification reaction for 30 seconds at 94° C., for 30 seconds at 65° C., and for 2 minutes at 72° C., was performed, and finally, incubation was performed for 2 minutes at 72° C. The amplifications of PCR were performed at 24 cycles for Lmx1a and Nurr1 and at 26 cycles for the other.

Figure 8:
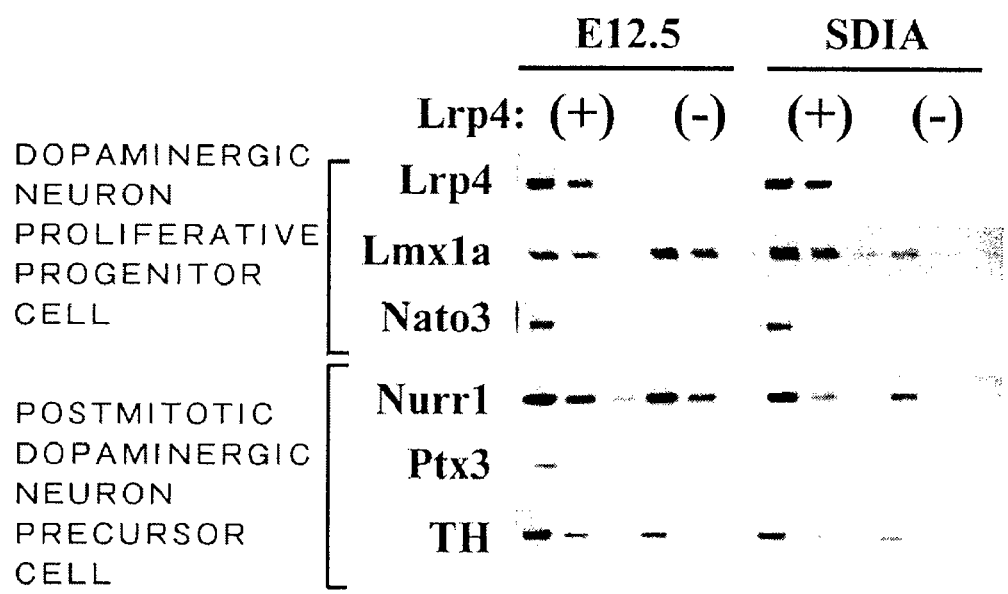
FIG. 8 shows the results of analyzing, by the RT-PCR method, expressions of Nato3 and other dopaminergic neuron marker genes in each of the dopaminergic neuron proliferative progenitor cells separated from the cells derived from the midbrain of a 12.5-day mouse embryo (E12.5) and the SDIA differentiation induction cells.

As a result, in the cells derived from the midbrain of the 12.5-day mouse embryo, mRNA of Nato3 was strongly expressed in a Lrp4-positive cell population (namely, dopaminergic neuron proliferative progenitor cells) (FIG. 8). Also, in the SDIA differentiation induction cells, mRNA of Nato3 was strongly expressed in the Lrp4-positive cell population (FIG. 8). Accordingly, it was revealed that mRNA of Nato3 is expressed in the dopaminergic neuron proliferative progenitor cell, in the SDIA differentiation induction cells as well as in the cells derived from the mouse embryonic midbrain.

Therefore, it was revealed that a Nato3 gene is a useful marker for discriminating not only the dopaminergic neuron proliferative progenitor cells derived from the embryonic midbrain but also the dopaminergic neuron proliferative progenitor cells induced to differentiate from ES cells in vitro.

The invention claimed is:

1. A kit for detecting or selecting a dopaminergic neuron proliferative progenitor cell, comprising a polynucleotide probe or polynucleotide primer for use in the detection or selection of a dopaminergic neuron proliferative progenitor cell, which can hybridize with a polynucleotide consisting of a nucleotide sequence of a mammalian Nato3 gene, or a complementary sequence thereto, wherein the polynucleotide probe or polynucleotide primer consists of a polynucleotide comprising a sequence of at least 10 contiguous nucleotides of a nucleotide sequence of the Nato3 gene, or a complementary sequence thereto, which further comprises a probe, a primer, a primer set, or an antibody, which can detect the expression of a dopaminergic neuron proliferative progenitor cell marker gene other than the Nato3 gene.

2. A kit for detecting or selecting a dopaminergic neuron proliferative progenitor cell, comprising:
   (i) a polynucleotide probe or polynucleotide primer for use in the detection or selection of a dopaminergic neuron proliferative progenitor cell, which can hybridize with a polynucleotide consisting of a nucleotide sequence of a mammalian Nato3 gene, or a complementary sequence thereto, wherein the polynucleotide probe or polynucleotide primer consists of a polynucleotide comprising a sequence of at least 10 contiguous nucleotides of a nucleotide sequence of the Nato3 gene, or a complementary sequence thereto; or
   (ii) a polynucleotide primer set comprising two or more kinds of the polynucleotide primers according (i),
   the kit further comprising a probe, a primer, a primer set, or an antibody, which can detect the expression of a dopaminergic neuron proliferative progenitor cell marker gene other than the Nato3 gene.

3. A method for detecting or selecting a dopaminergic neuron proliferative progenitor cell in a cell culture comprising the steps of:
   (a) contacting a polynucleotide derived from a cell sample from the culture to be tested, with a polynucleotide probe or polynucleotide primer which can hybridize with a polynucleotide consisting of a nucleotide sequence of a mammalian Nato3 gene, or a complementary sequence thereto, wherein the polynucleotide probe or polynucleotide primer consists of a polynucleotide comprising a sequence of at least 10 contiguous nucleotides of a nucleotide sequence of the Nato3 gene, or a complementary sequence thereto;
   (b) detecting a hybridization complex; and
   (c) determining the cell in which the hybridization complex is detected as a dopaminergic neuron proliferative progenitor cell.

4. The method of claim 3, wherein the nucleotide sequence of the Nato3 gene is a nucleotide sequence comprising a part or all of a nucleotide sequence selected from the group consisting of nucleotides 1-365 and 534-640 of SEQ ID NO:1, nucleotides 1-376 and 545-662 of SEQ ID NO:3, nucleotides 1-306 and 475-501 of SEQ ID NO:5, nucleotides 1-377 and 546-886 of SEQ ID NO:7, nucleotides 1-312 and 481-507 of SEQ ID NO:9, nucleotides 1-306 and 475-501 of SEQ ID NO:11, nucleotides 1-306 and 475-501 of SEQ ID NO:13, nucleotides 1-177 and 346-372 of SEQ ID NO:15, nucleotides 1-359 and 528-557 of SEQ ID NO:17, nucleotides 1-357 and 523-552 of SEQ ID NO:19.

5. The method of claim 3, wherein the polynucleotide that can hybridize has at least 15 base lengths.

6. The method of claim 3, wherein the cell culture is produced from embryonic stem (ES) cells induced to differentiate into dopaminergic neuron proliferative progenitor cells.

7. The method of claim 3, wherein the cell culture is a cell population obtained from a most ventral ventricular region of a midbrain of an 11.5 to 12.5-day embryo.

* * * * *

SEQUENCE LISTING

```
<160> NUMBER OF SEQ ID NOS: 46

<210> SEQ ID NO 1
<211> LENGTH: 640
<212> TYPE: DNA
<213> ORGANISM: Homo sapiens
<220> FEATURE:
<223> OTHER INFORMATION: nephew of atonal 3 (NATO3, Nato3), Fer3-like
      (Drosophila) (FERD3L), N-TWIST, basic
      helix-loop-helix (bHLH) transciption inhibitor
      cDNA
<220> FEATURE:
<221> NAME/KEY: CDS
<222> LOCATION: (60)...(560)
<223> OTHER INFORMATION: Nato3
```

```
<400> SEQUENCE: 1
accagcaacc tcgcccctcc ctgcggaaaa ccgatgagag gcagggccaa gccgaagcg      59 atg gcg gcc tat ccg gag agc tgc gtg gac act acg gtg ctg gac ttc     107
Met Ala Ala Tyr Pro Glu Ser Cys Val Asp Thr Thr Val Leu Asp Phe
1               5                  10                  15 gtc gca gac ctg tcc ctg gcc tcc ccg aga cgc cct ctc ctc tgc gac     155
Val Ala Asp Leu Ser Leu Ala Ser Pro Arg Arg Pro Leu Leu Cys Asp
            20                  25                  30 ttc gca ccc ggg gtc tcc ttg ggg gac cca gcc ctt gcg ctc cga gag     203
Phe Ala Pro Gly Val Ser Leu Gly Asp Pro Ala Leu Ala Leu Arg Glu
        35                  40                  45 gga aga ccc agg agg atg gcg cgg ttt gaa gag ggg gac cca gaa gaa     251
Gly Arg Pro Arg Arg Met Ala Arg Phe Glu Glu Gly Asp Pro Glu Glu
    50                  55                  60 gag gag tgc gaa gtg gac cag ggg gac gga gaa gag gag gaa gag         299
Glu Glu Cys Glu Val Asp Gln Gly Asp Gly Glu Glu Glu Glu Glu
65                  70                  75                  80 gag cgc gga aga ggt gtc tcc cta tta ggc cgc ccc aag agg aaa agg     347
Glu Arg Gly Arg Gly Val Ser Leu Leu Gly Arg Pro Lys Arg Lys Arg
                85                  90                  95 gtg atc acc tac gcc cag cgc cag gcc gcc aac atc cgc gaa agg aag     395
Val Ile Thr Tyr Ala Gln Arg Gln Ala Ala Asn Ile Arg Glu Arg Lys
            100                 105                 110 cgg atg ttc aac ctc aac gag gcc ttt gac cag ctg cgg agg aag gtg     443
Arg Met Phe Asn Leu Asn Glu Ala Phe Asp Gln Leu Arg Arg Lys Val
        115                 120                 125 ccc acg ttt gct tac gag aaa agg ctg tcc cgg atc gag acc ctc cgc     491
Pro Thr Phe Ala Tyr Glu Lys Arg Leu Ser Arg Ile Glu Thr Leu Arg
    130                 135                 140 ctg gcc atc gtc tat atc tcc ttc atg acc gag ctc ttg gag agc tgt     539
Leu Ala Ile Val Tyr Ile Ser Phe Met Thr Glu Leu Leu Glu Ser Cys
145                 150                 155                 160 gag aag aag gaa agc ggc tga gcctggtgtg gagagtctgc ccttcctcgt        590
Glu Lys Lys Glu Ser Gly
                165 ctggtagtgc tggggtgtgt caggaccggg cactgggtga ggctaaaggg              640

<210> SEQ ID NO 2
<211> LENGTH: 166
<212> TYPE: PRT
<213> ORGANISM: Homo sapiens
<220> FEATURE:
<223> OTHER INFORMATION: Nato3

<400> SEQUENCE: 2

Met Ala Ala Tyr Pro Glu Ser Cys Val Asp Thr Thr Val Leu Asp Phe
1               5                  10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Glu Cys Glu Val Asp Gln Gly Asp Gly Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110
```

```
Arg Met Phe Asn Leu Asn Glu Ala Phe Asp Gln Leu Arg Arg Lys Val
        115                 120                 125

Pro Thr Phe Ala Tyr Glu Lys Arg Leu Ser Arg Ile Glu Thr Leu Arg
130                 135                 140

Leu Ala Ile Val Tyr Ile Ser Phe Met Thr Glu Leu Leu Glu Ser Cys
145                 150                 155                 160

Glu Lys Lys Glu Ser Gly
            165

<210> SEQ ID NO 3
<211> LENGTH: 662
<212> TYPE: DNA
<213> ORGANISM: Homo sapiens
<220> FEATURE:
<223> OTHER INFORMATION: Nato3, N-TWIST, basic helix-loop-helix (bHLH)
      transciption inhibitor cDNA
<220> FEATURE:
<221> NAME/KEY: CDS
<222> LOCATION: (71)...(571)
<223> OTHER INFORMATION: Nato3

<400> SEQUENCE: 3
gaattcggct taccagcaac ctcgcccctc cctgcggaaa accgatgaga ggcagggcca        60
agccgaagcg atg gcg gcc tat ccg gag agc tgc gtg gac act acg gtg        109
            Met Ala Ala Tyr Pro Glu Ser Cys Val Asp Thr Thr Val
              1               5                  10 ctg gac ttc gtc gca gac ctg tcc ctg gcc tcc ccg aga cgc cct ctc        157
Leu Asp Phe Val Ala Asp Leu Ser Leu Ala Ser Pro Arg Arg Pro Leu
     15                  20                  25 ctc tgc gac ttc gca ccc ggg gtc tcc ttg ggg gac cca gcc ctt gcg        205
Leu Cys Asp Phe Ala Pro Gly Val Ser Leu Gly Asp Pro Ala Leu Ala
 30                  35                  40                  45 ctc cga gag gga aga ccc agg agg atg gcg cgg ttt gaa gag ggg gac        253
Leu Arg Glu Gly Arg Pro Arg Arg Met Ala Arg Phe Glu Glu Gly Asp
                 50                  55                  60 cca gaa gaa gag gag tgc gaa gtg gac cag ggg gac gga gaa gag gag        301
Pro Glu Glu Glu Glu Cys Glu Val Asp Gln Gly Asp Gly Glu Glu Glu
             65                  70                  75 gag gaa gag gag cgc gga aga ggt gtc tcc cta tta ggc cgc ccc aag        349
Glu Glu Glu Glu Arg Gly Arg Gly Val Ser Leu Leu Gly Arg Pro Lys
         80                  85                  90 agg aaa agg gtg atc acc tac gcc cag cgc cag gcc gcc aac atc cgc        397
Arg Lys Arg Val Ile Thr Tyr Ala Gln Arg Gln Ala Ala Asn Ile Arg
     95                 100                 105 gaa agg aag cgg atg ttc aac ctc aac gag gcc ttt gac cag ctg cgg        445
Glu Arg Lys Arg Met Phe Asn Leu Asn Glu Ala Phe Asp Gln Leu Arg
110                 115                 120                 125 agg aag gtg ccc acg ttt gct tac gag aaa agg ctg tcc cgg atc gag        493
Arg Lys Val Pro Thr Phe Ala Tyr Glu Lys Arg Leu Ser Arg Ile Glu
                130                 135                 140 acc ctc cgc ctg gcc atc gtc tat atc tcc ttc atg acc gag ctc ttg        541
Thr Leu Arg Leu Ala Ile Val Tyr Ile Ser Phe Met Thr Glu Leu Leu
            145                 150                 155 gag agc tgt gag aag aag gaa agc ggc tga gcctggtgtg agagtctgc            591
Glu Ser Cys Glu Lys Lys Glu Ser Gly
        160                 165 ccttcctcgt ctggtagtgc tggggtgtgt caggaccggg cactgggtga ggctaaaggg        651
aagccgaatt c                                                              662

<210> SEQ ID NO 4
```

-continued

```
<211> LENGTH: 166
<212> TYPE: PRT
<213> ORGANISM: Homo sapiens
<220> FEATURE:
<223> OTHER INFORMATION: Nato3

<400> SEQUENCE: 4

Met Ala Ala Tyr Pro Glu Ser Cys Val Asp Thr Thr Val Leu Asp Phe
1               5                  10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Cys Glu Val Asp Gln Gly Asp Gly Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Thr Phe Ala Tyr Glu Lys Arg Leu Ser Arg Ile Glu Thr Leu Arg
    130                 135                 140

Leu Ala Ile Val Tyr Ile Ser Phe Met Thr Glu Leu Leu Glu Ser Cys
145                 150                 155                 160

Glu Lys Lys Glu Ser Gly
                165

<210> SEQ ID NO 5
<211> LENGTH: 501
<212> TYPE: DNA
<213> ORGANISM: Homo sapiens
<220> FEATURE:
<223> OTHER INFORMATION: nephew of atonal 3 (NATO3, Nato3), Fer3-like
      (Drosophila) (FERD3L), N-TWIST, MGC95432, IMAGE
      7217007, basic helix-loop-helix (bHLH) transcription
      inhibitor cDNA
<220> FEATURE:
<221> NAME/KEY: CDS
<222> LOCATION: (1)...(501)
<223> OTHER INFORMATION: Nato3

<400> SEQUENCE: 5 atg gcg gcc tat ccg gag agc tgc gtg gac act acg gtg ctg gac ttc      48
Met Ala Ala Tyr Pro Glu Ser Cys Val Asp Thr Thr Val Leu Asp Phe
1               5                  10                  15 gtc gca gac ctg tcc ctg gcc tcc ccg aga cgc cct ctc ctc tgc gac      96
Val Ala Asp Leu Ser Leu Ala Ser Pro Arg Arg Pro Leu Leu Cys Asp
            20                  25                  30 ttc gca ccc ggg gtc tcc ttg ggg gac cca gcc ctt gcg ctc cga gag     144
Phe Ala Pro Gly Val Ser Leu Gly Asp Pro Ala Leu Ala Leu Arg Glu
        35                  40                  45 gga aga ccc agg agg atg gcg cgg ttt gaa gag ggg gac cca gaa gaa     192
Gly Arg Pro Arg Arg Met Ala Arg Phe Glu Glu Gly Asp Pro Glu Glu
    50                  55                  60 gag gag tgc gaa gtg gac cag ggg gac gga gaa gag gag gag gaa gag     240
Glu Glu Cys Glu Val Asp Gln Gly Asp Gly Glu Glu Glu Glu Glu Glu
65                  70                  75                  80 gag cgc gga aga ggt gtc tcc cta tta ggc cgc ccc aag agg aaa agg     288
Glu Arg Gly Arg Gly Val Ser Leu Leu Gly Arg Pro Lys Arg Lys Arg
```

```
                       85                  90                  95
gtg atc acc tac gcc cag cgc cag gcc gcc aac atc cgc gaa agg aag        336
Val Ile Thr Tyr Ala Gln Arg Gln Ala Ala Asn Ile Arg Glu Arg Lys
        100                 105                 110 cgg atg ttc aac ctc aac gag gcc ttt gac cag ctg cgg agg aag gtg        384
Arg Met Phe Asn Leu Asn Glu Ala Phe Asp Gln Leu Arg Arg Lys Val
        115                 120                 125 ccc acg ttt gct tac gag aaa agg ctg tcc cgg atc gag acc ctc cgc        432
Pro Thr Phe Ala Tyr Glu Lys Arg Leu Ser Arg Ile Glu Thr Leu Arg
        130                 135                 140 ctg gcc atc gtc tat atc tcc ttc atg acc gag ctc ttg gag agc tgt        480
Leu Ala Ile Val Tyr Ile Ser Phe Met Thr Glu Leu Leu Glu Ser Cys
145                 150                 155                 160 gag aag aag gaa agc ggc tga                                            501
Glu Lys Lys Glu Ser Gly
            165

<210> SEQ ID NO 6
<211> LENGTH: 166
<212> TYPE: PRT
<213> ORGANISM: Homo sapiens
<220> FEATURE:
<223> OTHER INFORMATION: Nato3

<400> SEQUENCE: 6

Met Ala Ala Tyr Pro Glu Ser Cys Val Asp Thr Thr Val Leu Asp Phe
1               5                   10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Glu Cys Glu Val Asp Gln Asp Gly Glu Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Thr Phe Ala Tyr Glu Lys Arg Leu Ser Arg Ile Glu Thr Leu Arg
    130                 135                 140

Leu Ala Ile Val Tyr Ile Ser Phe Met Thr Glu Leu Leu Glu Ser Cys
145                 150                 155                 160

Glu Lys Lys Glu Ser Gly
            165

<210> SEQ ID NO 7
<211> LENGTH: 886
<212> TYPE: DNA
<213> ORGANISM: Mus musculus
<220> FEATURE:
<223> OTHER INFORMATION: nephew of atonal 3 (Mnato3, Nato3), Fer3-like
      (Drosophila) (FERD3L, fer3), N-TWIST, MGC130442,
      basic helix-loop-helix (bHLH) transcription inhibitor
      cDNA
<220> FEATURE:
<221> NAME/KEY: CDS
<222> LOCATION: (66)...(572)
<223> OTHER INFORMATION: Nato3
```

<400> SEQUENCE: 7

```
accaaggagc tctatcggca gctatgccat tcctgcaaga aaatcggtga gatagacgct        60 gagtg atg gcc gcc tat cca gag agc tgc ttg gat gct acc gtg ctg aac       110
      Met Ala Ala Tyr Pro Glu Ser Cys Leu Asp Ala Thr Val Leu Asn
      1               5                  10                  15 ttc gta gca gat ctc tct ctg gcc tct ccc aga cac cct ctt ctc tgc          158
Phe Val Ala Asp Leu Ser Leu Ala Ser Pro Arg His Pro Leu Leu Cys
                20                  25                  30 gag ttc cca cct ggg gtc cct ttt ggg gac cga aca ctg ggg tac aga          206
Glu Phe Pro Pro Gly Val Pro Phe Gly Asp Arg Thr Leu Gly Tyr Arg
            35                  40                  45 gag gga aga cct ggg aga ctg tcg cag ttt gat gaa aga tat cag gaa          254
Glu Gly Arg Pro Gly Arg Leu Ser Gln Phe Asp Glu Arg Tyr Gln Glu
        50                  55                  60 gta gag ggg gac gaa gtg gaa tat gag gac cca gaa gag gag gaa gag          302
Val Glu Gly Asp Glu Val Glu Tyr Glu Asp Pro Glu Glu Glu Glu Glu
65                  70                  75 gag gga gag ggg cgc ggc aga gta gca tcc ttg ctg ggc cgc ccc aaa          350
Glu Gly Glu Gly Arg Gly Arg Val Ala Ser Leu Leu Gly Arg Pro Lys
80                  85                  90                  95 aga aaa aga gtt att act tat gcc cag cgc cag gcc gcc aac att cgc          398
Arg Lys Arg Val Ile Thr Tyr Ala Gln Arg Gln Ala Ala Asn Ile Arg
                100                 105                 110 gag agg aag agg atg ttc aac cta aac gag gcc ttc gac cag ctg cgc          446
Glu Arg Lys Arg Met Phe Asn Leu Asn Glu Ala Phe Asp Gln Leu Arg
            115                 120                 125 aga aag gta ccc acc ttc gct tat gag aag aga ctg tcg agg atc gag          494
Arg Lys Val Pro Thr Phe Ala Tyr Glu Lys Arg Leu Ser Arg Ile Glu
        130                 135                 140 acc ctc cgc ttg gcc atc gtc tac att tcc ttc atg acc gag ctc ctg          542
Thr Leu Arg Leu Ala Ile Val Tyr Ile Ser Phe Met Thr Glu Leu Leu
145                 150                 155 cag agc aag gag gaa aag gag gcc agc tga gcggggaggg gtgagcccaa            592
Gln Ser Lys Glu Glu Lys Glu Ala Ser
160                 165 gagacactcc cccgcctcat cgtgcttggc ggggtgcgtc tggaaggcag aggggccgct       652
ggccttctga ggcggggttt gagatggtaa actccccact cgcggcagct ctgcagtgaa       712
taagttgggg atccggcaca ataagggtct agctgggcag gttgggagtt cccggggtca       772
aggatttagg gagttagagc ttcttgcttg gagcaggtgg gaaactggtc tgctcctcca       832
cggacctctg gtgatctctc ctccttgctc cttttcaaca gtagaataa taaa              886
```

<210> SEQ ID NO 8
<211> LENGTH: 168
<212> TYPE: PRT
<213> ORGANISM: Mus musculus
<220> FEATURE:
<223> OTHER INFORMATION: Nato3

<400> SEQUENCE: 8

```
Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60
```

```
Glu Gly Asp Glu Val Glu Tyr Glu Asp Pro Glu Glu Glu Glu Glu
 65                  70                  75                  80

Gly Glu Gly Arg Gly Arg Val Ala Ser Leu Leu Gly Arg Pro Lys Arg
                 85                  90                  95

Lys Arg Val Ile Thr Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Thr Phe Ala Tyr Glu Lys Arg Leu Ser Arg Ile Glu Thr
    130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 9
<211> LENGTH: 507
<212> TYPE: DNA
<213> ORGANISM: Mus musculus
<220> FEATURE:
<223> OTHER INFORMATION: nephew of atonal 3 (NATO3, Nato3), Fer3-like
      (Drosophila) (FERD3L, fer3), N-TWIST, basic
      helix-loop-helix (bHLH) transcription inhibitor CDS
<220> FEATURE:
<221> NAME/KEY: CDS
<222> LOCATION: (1)...(507)
<223> OTHER INFORMATION: Nato3

<400> SEQUENCE: 9 atg gcc gcc tat cca gag agc tgc ttg gat gct acc gtg ctg aac ttc      48
Met Ala Ala Tyr Pro Glu Ser Cys Leu Asp Ala Thr Val Leu Asn Phe
1               5                  10                  15 gta gca gat ctc tct ctg gcc tct ccc aga cac cct ctt ctc tgc gag      96
Val Ala Asp Leu Ser Leu Ala Ser Pro Arg His Pro Leu Leu Cys Glu
            20                  25                  30 ttc cca cct ggg gtc cct ttt ggg gac cga aca ctg ggg tac aga gag     144
Phe Pro Pro Gly Val Pro Phe Gly Asp Arg Thr Leu Gly Tyr Arg Glu
        35                  40                  45 gga aga cct ggg aga ctg tcg cag ttt gat gaa aga tat cag gaa gta     192
Gly Arg Pro Gly Arg Leu Ser Gln Phe Asp Glu Arg Tyr Gln Glu Val
    50                  55                  60 gag ggg gac gaa gtg gaa tat gag gac cca gaa gag gag gaa gag gag     240
Glu Gly Asp Glu Val Glu Tyr Glu Asp Pro Glu Glu Glu Glu Glu Glu
65                  70                  75                  80 gga gag ggg cgc ggc aga gta gca tcc ttg ctg ggc cgc ccc aaa aga     288
Gly Glu Gly Arg Gly Arg Val Ala Ser Leu Leu Gly Arg Pro Lys Arg
                85                  90                  95 aaa aga gtt att act tat gcc cag cgc cag gcc gcc aac att cgc gag     336
Lys Arg Val Ile Thr Tyr Ala Gln Arg Gln Ala Ala Asn Ile Arg Glu
            100                 105                 110 agg aag agg atg ttc aac cta aac gag gcc ttc gac cag ctg cgc aga     384
Arg Lys Arg Met Phe Asn Leu Asn Glu Ala Phe Asp Gln Leu Arg Arg
        115                 120                 125 aag gta ccc acc ttc gct tat gag aag aga ctg tcg agg atc gag acc     432
Lys Val Pro Thr Phe Ala Tyr Glu Lys Arg Leu Ser Arg Ile Glu Thr
    130                 135                 140 ctc cgc ttg gcc atc gtc tac att tcc ttc atg acc gag ctc ctg cag     480
Leu Arg Leu Ala Ile Val Tyr Ile Ser Phe Met Thr Glu Leu Leu Gln
145                 150                 155                 160 agc aag gag gaa aag gag gcc agc tga                                  507
Ser Lys Glu Glu Lys Glu Ala Ser
                165
```

<210> SEQ ID NO 10
<211> LENGTH: 168
<212> TYPE: PRT
<213> ORGANISM: Mus musculus
<220> FEATURE:
<223> OTHER INFORMATION: Nato3

<400> SEQUENCE: 10

```
Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Thr Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Thr Phe Ala Tyr Glu Lys Arg Leu Ser Arg Ile Glu Thr
    130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165
```

<210> SEQ ID NO 11
<211> LENGTH: 501
<212> TYPE: DNA
<213> ORGANISM: Rattus norvegicus
<220> FEATURE:
<223> OTHER INFORMATION: nephew of atonal 3 (Nato3), Fer3-like
      (Drosophila) (Ferd3l), basic helix-loop-helix (bHLH) transcription
      inhibitor cDNA
<220> FEATURE:
<221> NAME/KEY: CDS
<222> LOCATION: (1)...(501)
<223> OTHER INFORMATION: Nato3

<400> SEQUENCE: 11

```
atg gcc gcc tat cca gag agc tgc ttg gac gct aac gtg ctg aac ttc      48
Met Ala Ala Tyr Pro Glu Ser Cys Leu Asp Ala Asn Val Leu Asn Phe
1               5                   10                  15 gta gca gat ctc tct ctg gcc tct ccc aga cac cct ttt ctc tgc gag      96
Val Ala Asp Leu Ser Leu Ala Ser Pro Arg His Pro Phe Leu Cys Glu
            20                  25                  30 ttc cca cct ggg gtc cct ttt gag gac caa aca ctg ggg ttc aga gaa     144
Phe Pro Pro Gly Val Pro Phe Glu Asp Gln Thr Leu Gly Phe Arg Glu
        35                  40                  45 gga agg ggg ctg ttg cag ttt gag gga aga tac cag gaa gta gag ggg     192
Gly Arg Gly Leu Leu Gln Phe Glu Gly Arg Tyr Gln Glu Val Glu Gly
    50                  55                  60 gga gaa gtg gac tat gag gac ccg gaa gag gag gaa gag gag gga gag     240
Gly Glu Val Asp Tyr Glu Asp Pro Glu Glu Glu Glu Glu Glu Gly Glu
65                  70                  75                  80
```

```
ggg cgc ggc cga gta gca tcc ttg ctg ggc cgc ccc aaa agg aaa aga      288
Gly Arg Gly Arg Val Ala Ser Leu Leu Gly Arg Pro Lys Arg Lys Arg
                85                  90                  95 gtc atc act tat gcc cag cgc cag gcc gcc aac att cgc gag aga aag      336
Val Ile Thr Tyr Ala Gln Arg Gln Ala Ala Asn Ile Arg Glu Arg Lys
            100                 105                 110 agg atg ttt aac cta aac gag gcc ttc gac cag ctg cgc agg aag gtg      384
Arg Met Phe Asn Leu Asn Glu Ala Phe Asp Gln Leu Arg Arg Lys Val
        115                 120                 125 ccc acc ttc gct tat gag aag agg ctg tcc agg atc gag acc ctc cgc      432
Pro Thr Phe Ala Tyr Glu Lys Arg Leu Ser Arg Ile Glu Thr Leu Arg
    130                 135                 140 ttg gcc atc gtc tac att tct ttc atg acc gag ctc ctg cag agc aag      480
Leu Ala Ile Val Tyr Ile Ser Phe Met Thr Glu Leu Leu Gln Ser Lys
145                 150                 155                 160 gag gaa aag gag gcc agc tga                                          501
Glu Glu Lys Glu Ala Ser
                165

<210> SEQ ID NO 12
<211> LENGTH: 166
<212> TYPE: PRT
<213> ORGANISM: Rattus norvegicus
<220> FEATURE:
<223> OTHER INFORMATION: Nato3

<400> SEQUENCE: 12

Met Ala Ala Tyr Pro Glu Ser Cys Leu Asp Ala Asn Val Leu Asn Phe
1               5                   10                  15

Val Ala Asp Leu Ser Leu Ala Ser Pro Arg His Pro Phe Leu Cys Glu
            20                  25                  30

Phe Pro Pro Gly Val Pro Phe Glu Asp Gln Thr Leu Gly Phe Arg Glu
        35                  40                  45

Gly Arg Gly Leu Leu Gln Phe Glu Gly Arg Tyr Gln Glu Val Glu Gly
    50                  55                  60

Gly Glu Val Asp Tyr Glu Asp Pro Glu Glu Glu Glu Glu Gly Glu
65                  70                  75                  80

Gly Arg Gly Arg Val Ala Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Thr Phe Ala Tyr Glu Lys Arg Leu Ser Arg Ile Glu Thr Leu Arg
    130                 135                 140

Leu Ala Ile Val Tyr Ile Ser Phe Met Thr Glu Leu Leu Gln Ser Lys
145                 150                 155                 160

Glu Glu Lys Glu Ala Ser
                165

<210> SEQ ID NO 13
<211> LENGTH: 501
<212> TYPE: DNA
<213> ORGANISM: Pan troglodytes
<220> FEATURE:
<223> OTHER INFORMATION: nephew of atonal 3 (Nato3), LOC472301, basic
      helix-loop-helix (bHLH) transcription inhibitor cDNA
<220> FEATURE:
<221> NAME/KEY: CDS
<222> LOCATION: (1)...(501)
<223> OTHER INFORMATION: Nato3
```

<400> SEQUENCE: 13

```
atg gcg gcc tat ccg gag agc tgc gtg gac acg acg gtg ctg gac ttc        48
Met Ala Ala Tyr Pro Glu Ser Cys Val Asp Thr Thr Val Leu Asp Phe
1               5                   10                  15 gtc gca gac ctg tcc ctg gcc tcc ccg aga cgc cct ctc ctc tgc gac        96
Val Ala Asp Leu Ser Leu Ala Ser Pro Arg Arg Pro Leu Leu Cys Asp
                20                  25                  30 ttc gca ccc ggg gtc tcc ttg ggg gac cca gcc ctt gcg ctc cga gag       144
Phe Ala Pro Gly Val Ser Leu Gly Asp Pro Ala Leu Ala Leu Arg Glu
            35                  40                  45 gga aga ccc agg agg atg gcg cgg ttt gaa gag ggg gac cca gaa gaa       192
Gly Arg Pro Arg Arg Met Ala Arg Phe Glu Glu Gly Asp Pro Glu Glu
        50                  55                  60 gag gag tgc gaa gtg gac cag ggg gac gga gaa gag gag gag gaa gag       240
Glu Glu Cys Glu Val Asp Gln Gly Asp Gly Glu Glu Glu Glu Glu Glu
65                  70                  75                  80 gag cgc gga aga ggt gtc tcc cta tta ggc cgc ccc aag agg aaa agg       288
Glu Arg Gly Arg Gly Val Ser Leu Leu Gly Arg Pro Lys Arg Lys Arg
                85                  90                  95 gtg atc acc tac gcc cag cgc cag gcc gcc aac atc cgc gaa agg aag       336
Val Ile Thr Tyr Ala Gln Arg Gln Ala Ala Asn Ile Arg Glu Arg Lys
                100                 105                 110 agg atg ttc aac ctc aac gag gcc ttt gac cag ctg cgg agg aag gtg       384
Arg Met Phe Asn Leu Asn Glu Ala Phe Asp Gln Leu Arg Arg Lys Val
            115                 120                 125 ccc acg ttt gct tac gag aaa agg ctg tcc cgg atc gag acc ctc cgc       432
Pro Thr Phe Ala Tyr Glu Lys Arg Leu Ser Arg Ile Glu Thr Leu Arg
        130                 135                 140 ctg gcc atc gtc tac atc tcc ttc atg acc gag ctc ttg gag agc tgt       480
Leu Ala Ile Val Tyr Ile Ser Phe Met Thr Glu Leu Leu Glu Ser Cys
145                 150                 155                 160 gag aag aag gaa agc ggc tga                                           501
Glu Lys Lys Glu Ser Gly
                165
```

<210> SEQ ID NO 14
<211> LENGTH: 166
<212> TYPE: PRT
<213> ORGANISM: Pan troglodytes
<220> FEATURE:
<223> OTHER INFORMATION: Nato3

<400> SEQUENCE: 14

```
Met Ala Ala Tyr Pro Glu Ser Cys Val Asp Thr Thr Val Leu Asp Phe
1               5                   10                  15

Val Ala Asp Leu Ser Leu Ala Ser Pro Arg Arg Pro Leu Leu Cys Asp
                20                  25                  30

Phe Ala Pro Gly Val Ser Leu Gly Asp Pro Ala Leu Ala Leu Arg Glu
            35                  40                  45

Gly Arg Pro Arg Arg Met Ala Arg Phe Glu Glu Gly Asp Pro Glu Glu
        50                  55                  60

Glu Glu Cys Glu Val Asp Gln Gly Asp Gly Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Thr Tyr Ala Gln Arg Gln Ala Ala Asn Ile Arg Glu Arg Lys
                100                 105                 110

Arg Met Phe Asn Leu Asn Glu Ala Phe Asp Gln Leu Arg Arg Lys Val
            115                 120                 125
```

```
Pro Thr Phe Ala Tyr Glu Lys Arg Leu Ser Arg Ile Glu Thr Leu Arg
        130                 135                 140

Leu Ala Ile Val Tyr Ile Ser Phe Met Thr Glu Leu Leu Glu Ser Cys
145                 150                 155                 160

Glu Lys Lys Glu Ser Gly
            165

<210> SEQ ID NO 15
<211> LENGTH: 372
<212> TYPE: DNA
<213> ORGANISM: Canis familiaris
<220> FEATURE:
<223> OTHER INFORMATION: nephew of atonal 3 (Nato3), LOC482340, basic
      helix-loop-helix (bHLH) transciption inhibitor cDNA
<220> FEATURE:
<221> NAME/KEY: CDS
<222> LOCATION: (1)...(372)
<223> OTHER INFORMATION: Nato3

<400> SEQUENCE: 15 atg gcg gcc tac ccg gag ggc tgc gtg gac gcc acc gtg ctg gac ttc      48
Met Ala Ala Tyr Pro Glu Gly Cys Val Asp Ala Thr Val Leu Asp Phe
1               5                   10                  15 gtc gcg gac ctg tcc ctg gac tcc ccc ggg cac ccg ctc ctc tgc gac      96
Val Ala Asp Leu Ser Leu Asp Ser Pro Gly His Pro Leu Leu Cys Asp
            20                  25                  30 ttc gca ccc ggg ctt ccc ttt ggg gac cgg gac ctt gtg ctc cga gag     144
Phe Ala Pro Gly Leu Pro Phe Gly Asp Arg Asp Leu Val Leu Arg Glu
        35                  40                  45 gga agg cgc aga agg ctg gca ggc ttt gag gag cgc cag gcg gcc aac     192
Gly Arg Arg Arg Arg Leu Ala Gly Phe Glu Glu Arg Gln Ala Ala Asn
    50                  55                  60 atc cgc gag agg aag cgg atg ttc aac ctc aac gag gcc ttc gac cag     240
Ile Arg Glu Arg Lys Arg Met Phe Asn Leu Asn Glu Ala Phe Asp Gln
65                  70                  75                  80 ctg cga cgg aag gtg ccc acc ttt gct tac gag aag agg ctg tcc cgg     288
Leu Arg Arg Lys Val Pro Thr Phe Ala Tyr Glu Lys Arg Leu Ser Arg
                85                  90                  95 atc gag acc cta cgc ctg gcc atc gtc tac att tcc ttc atg acc gag     336
Ile Glu Thr Leu Arg Leu Ala Ile Val Tyr Ile Ser Phe Met Thr Glu
            100                 105                 110 ctc ctg gag agc tgc gca aag aaa gaa acc ggc tga                     372
Leu Leu Glu Ser Cys Ala Lys Lys Glu Thr Gly
        115                 120

<210> SEQ ID NO 16
<211> LENGTH: 123
<212> TYPE: PRT
<213> ORGANISM: Canis familiaris
<220> FEATURE:
<223> OTHER INFORMATION: Nato3

<400> SEQUENCE: 16

Met Ala Ala Tyr Pro Glu Gly Cys Val Asp Ala Thr Val Leu Asp Phe
1               5                   10                  15

Val Ala Asp Leu Ser Leu Asp Ser Pro Gly His Pro Leu Leu Cys Asp
            20                  25                  30

Phe Ala Pro Gly Leu Pro Phe Gly Asp Arg Asp Leu Val Leu Arg Glu
        35                  40                  45

Gly Arg Arg Arg Arg Leu Ala Gly Phe Glu Glu Arg Gln Ala Ala Asn
    50                  55                  60

Ile Arg Glu Arg Lys Arg Met Phe Asn Leu Asn Glu Ala Phe Asp Gln
65                  70                  75                  80
```

```
Leu Arg Arg Lys Val Pro Thr Phe Ala Tyr Glu Lys Arg Leu Ser Arg
                 85                  90                  95

Ile Glu Thr Leu Arg Leu Ala Ile Val Tyr Ile Ser Phe Met Thr Glu
            100                 105                 110

Leu Leu Glu Ser Cys Ala Lys Lys Glu Thr Gly
        115                 120

<210> SEQ ID NO 17
<211> LENGTH: 557
<212> TYPE: DNA
<213> ORGANISM: Bos taurus
<220> FEATURE:
<223> OTHER INFORMATION: nephew of atonal 3 (Nato3), LOC538985, basic
      helix-loop-helix (bHLH) transciption inhibitor cDNA
<220> FEATURE:
<221> NAME/KEY: CDS
<222> LOCATION: (57)...(551)
<223> OTHER INFORMATION: Nato3

<400> SEQUENCE: 17
accaggcttg ccccctcccctt caataaattt atgagacgca gggccaagca gacgcg atg    59
                                                              Met
                                                                1 gca gcc ttt ccc gag agc tgc gtg gac gcc acc gtc ctg gac ttc gtc       107
Ala Ala Phe Pro Glu Ser Cys Val Asp Ala Thr Val Leu Asp Phe Val
        5                   10                  15 gca gac cta tcc cta gcc tcc ccg ggg cac cct ctc ctc tgc gac ttg       155
Ala Asp Leu Ser Leu Ala Ser Pro Gly His Pro Leu Leu Cys Asp Leu
            20                  25                  30 aca cct agg gtc ccc tat ggg aac cac cag gac ctt gtg ctc cga gac       203
Thr Pro Arg Val Pro Tyr Gly Asn His Gln Asp Leu Val Leu Arg Asp
        35                  40                  45 gga aga ccc agg agt ctg gcg cgt ttt gag gaa gag gat cca gaa gaa       251
Gly Arg Pro Arg Ser Leu Ala Arg Phe Glu Glu Glu Asp Pro Glu Glu
 50                 55                  60                  65 gag gag ggg gaa gga gaa gag ggg gaa aac gag gag gaa gag gag cac       299
Glu Glu Gly Glu Gly Glu Glu Gly Glu Asn Glu Glu Glu Glu Glu His
                70                  75                  80 ggg aga ggc gcc tcc cta ctg ggc cgc ccc aag agg aaa aga gtg atc       347
Gly Arg Gly Ala Ser Leu Leu Gly Arg Pro Lys Arg Lys Arg Val Ile
            85                  90                  95 acc tac gcc cag cgc caa gca gcc aac atc cgc gag agg aag cgg atg       395
Thr Tyr Ala Gln Arg Gln Ala Ala Asn Ile Arg Glu Arg Lys Arg Met
        100                 105                 110 ttc aac ctc aac gag gcc ttc gat cag ctg cgg agg aag gtg ccc act       443
Phe Asn Leu Asn Glu Ala Phe Asp Gln Leu Arg Arg Lys Val Pro Thr
    115                 120                 125 ttc gct tac gag aag agg ctc tcc cgg atc gag act cta cgc ctg gcc       491
Phe Ala Tyr Glu Lys Arg Leu Ser Arg Ile Glu Thr Leu Arg Leu Ala
130                 135                 140                 145 att gtc tac atc tcc ttc atg acc gag ctc ttg gag agc ttg gag aag       539
Ile Val Tyr Ile Ser Phe Met Thr Glu Leu Leu Glu Ser Leu Glu Lys
                150                 155                 160 gaa aga gac tga gccagg                                                557
Glu Arg Asp <210> SEQ ID NO 18
<211> LENGTH: 164
<212> TYPE: PRT
<213> ORGANISM: Bos taurus
<220> FEATURE:
<223> OTHER INFORMATION: Nato3
```

<400> SEQUENCE: 18

```
Met Ala Ala Phe Pro Glu Ser Cys Val Asp Thr Val Leu Asp Phe
1               5                   10                  15

Val Ala Asp Leu Ser Leu Ala Ser Pro Gly His Pro Leu Leu Cys Asp
            20                  25                  30

Leu Thr Pro Arg Val Pro Tyr Gly Asn His Gln Asp Leu Val Leu Arg
            35                  40                  45

Asp Gly Arg Pro Arg Ser Leu Ala Arg Phe Glu Glu Asp Pro Glu
    50                  55                  60

Glu Glu Glu Gly Glu Gly Glu Gly Glu Asn Glu Glu Glu Glu Glu
65                  70                  75                  80

His Gly Arg Gly Ala Ser Leu Leu Gly Arg Pro Lys Arg Lys Arg Val
                85                  90                  95

Ile Thr Tyr Ala Gln Arg Gln Ala Ala Asn Ile Arg Glu Arg Lys Arg
            100                 105                 110

Met Phe Asn Leu Asn Glu Ala Phe Asp Gln Leu Arg Arg Lys Val Pro
            115                 120                 125

Thr Phe Ala Tyr Glu Lys Arg Leu Ser Arg Ile Glu Thr Leu Arg Leu
        130                 135                 140

Ala Ile Val Tyr Ile Ser Phe Met Thr Glu Leu Leu Glu Ser Leu Glu
145                 150                 155                 160

Lys Glu Arg Asp
```

<210> SEQ ID NO 19
<211> LENGTH: 552
<212> TYPE: DNA
<213> ORGANISM: Gallus gallus
<220> FEATURE:
<223> OTHER INFORMATION: nephew of atonal 3 (Nato3), LOC428429, basic
      helix-loop-helix (bHLH) transcription inhibitor cDNA
<220> FEATURE:
<221> NAME/KEY: CDS
<222> LOCATION: (1)...(552)
<223> OTHER INFORMATION: Nato3

<400> SEQUENCE: 19

```
atg tca gcc ggc ctc ttc ccg gcc cac cgg cgc ccg gag ctg ctc cgc      48
Met Ser Ala Gly Leu Phe Pro Ala His Arg Arg Pro Glu Leu Leu Arg
1               5                   10                  15 ggc aca gct ccg ccg ctc ccc tgc ccg gag cgg ctg ctg ggt gcc tcg      96
Gly Thr Ala Pro Pro Leu Pro Cys Pro Glu Arg Leu Leu Gly Ala Ser
            20                  25                  30 gtg ctg ggt ttc gtg gcc gac atc tcg ctg gga gcc ccc cag agc tca     144
Val Leu Gly Phe Val Ala Asp Ile Ser Leu Gly Ala Pro Gln Ser Ser
        35                  40                  45 tct cgg gcc gga ccg agc ctg ggg tta acc tcc gag cct ccc ttc ggg     192
Ser Arg Ala Gly Pro Ser Leu Gly Leu Thr Ser Glu Pro Pro Phe Gly
    50                  55                  60 gac aga acc ctg tcg ctg cgg gag ggg atg gcc cgg ggg ttg cct ttg     240
Asp Arg Thr Leu Ser Leu Arg Glu Gly Met Ala Arg Gly Leu Pro Leu
65                  70                  75                  80 gct gcc ttc gga gac ggg gat ctc gaa gac gag gaa gaa gag gaa gaa     288
Ala Ala Phe Gly Asp Gly Asp Leu Glu Asp Glu Glu Glu Glu Glu Glu
                85                  90                  95 gag gag aga atg cgg agc gct tcc cta ctg gac aga ccc agg aga aag     336
Glu Glu Arg Met Arg Ser Ala Ser Leu Leu Asp Arg Pro Arg Arg Lys
            100                 105                 110 cgg gtt atc acc tac gcc cag cgc cag gca gcc aac atc cgg gag agg     384
Arg Val Ile Thr Tyr Ala Gln Arg Gln Ala Ala Asn Ile Arg Glu Arg
            115                 120                 125
```

```
aag agg atg ttc aac ctc aac gag gcg ttc gac cag ctg agg aag aag      432
Lys Arg Met Phe Asn Leu Asn Glu Ala Phe Asp Gln Leu Arg Lys Lys
        130                 135                 140 gtg ccc acc ttc gcc tac gag aag cgg ctc tcc cgg ata gag acc ttg      480
Val Pro Thr Phe Ala Tyr Glu Lys Arg Leu Ser Arg Ile Glu Thr Leu
145                 150                 155                 160 cgc ctg gcc atc gtg tac atc tcc ttc atg acc gag ctc ctg aac ggc      528
Arg Leu Ala Ile Val Tyr Ile Ser Phe Met Thr Glu Leu Leu Asn Gly
                165                 170                 175 tgc agc agg cag gag gcg agc tag                                      552
Cys Ser Arg Gln Glu Ala Ser
            180
```

<210> SEQ ID NO 20
<211> LENGTH: 183
<212> TYPE: PRT
<213> ORGANISM: Gallus gallus
<220> FEATURE:
<223> OTHER INFORMATION: Nato3

<400> SEQUENCE: 20

```
Met Ser Ala Gly Leu Phe Pro Ala His Arg Arg Pro Glu Leu Leu Arg
1               5                   10                  15

Gly Thr Ala Pro Pro Leu Pro Cys Pro Glu Arg Leu Leu Gly Ala Ser
            20                  25                  30

Val Leu Gly Phe Val Ala Asp Ile Ser Leu Gly Ala Pro Gln Ser Ser
        35                  40                  45

Ser Arg Ala Gly Pro Ser Leu Gly Leu Thr Ser Glu Pro Pro Phe Gly
    50                  55                  60

Asp Arg Thr Leu Ser Leu Arg Glu Gly Met Ala Arg Gly Leu Pro Leu
65                  70                  75                  80

Ala Ala Phe Gly Asp Gly Asp Leu Glu Asp Glu Glu Glu Glu Glu Glu
                85                  90                  95

Glu Glu Arg Met Arg Ser Ala Ser Leu Leu Asp Arg Pro Arg Arg Lys
            100                 105                 110

Arg Val Ile Thr Tyr Ala Gln Arg Gln Ala Ala Asn Ile Arg Glu Arg
        115                 120                 125

Lys Arg Met Phe Asn Leu Asn Glu Ala Phe Asp Gln Leu Arg Lys Lys
    130                 135                 140

Val Pro Thr Phe Ala Tyr Glu Lys Arg Leu Ser Arg Ile Glu Thr Leu
145                 150                 155                 160

Arg Leu Ala Ile Val Tyr Ile Ser Phe Met Thr Glu Leu Leu Asn Gly
                165                 170                 175

Cys Ser Arg Gln Glu Ala Ser
            180
```

<210> SEQ ID NO 21
<211> LENGTH: 26
<212> TYPE: DNA
<213> ORGANISM: Artificial Sequence
<220> FEATURE:
<223> OTHER INFORMATION: synthetic RT-PCR amplification primer ad2S

<400> SEQUENCE: 21
cagctccaca acctacatca ttccgt                                          26

<210> SEQ ID NO 22
<211> LENGTH: 12
<212> TYPE: DNA
<213> ORGANISM: Artificial Sequence

```
<220> FEATURE:
<223> OTHER INFORMATION: synthetic RT-PCR amplification primer ad2A

<400> SEQUENCE: 22
acggaatgat gt                                                          12

<210> SEQ ID NO 23
<211> LENGTH: 26
<212> TYPE: DNA
<213> ORGANISM: Artificial Sequence
<220> FEATURE:
<223> OTHER INFORMATION: synthetic Lrp4 marker for dopaminergic neuron
      proliferative progenitor cells PCR amplification
      primer

<400> SEQUENCE: 23
tagtctacca ctgctcgact gtaacg                                           26

<210> SEQ ID NO 24
<211> LENGTH: 26
<212> TYPE: DNA
<213> ORGANISM: Artificial Sequence
<220> FEATURE:
<223> OTHER INFORMATION: synthetic Lrp4 marker for dopaminergic neuron
      proliferative progenitor cells PCR amplification
      primer

<400> SEQUENCE: 24
cagagtgaac ccagtggaca tatctg                                           26

<210> SEQ ID NO 25
<211> LENGTH: 26
<212> TYPE: DNA
<213> ORGANISM: Artificial Sequence
<220> FEATURE:
<223> OTHER INFORMATION: synthetic DAT marker for dopaminergic neuron
      cells PCR amplification primer

<400> SEQUENCE: 25
cagaatcctg tgctcacggt agttgc                                           26

<210> SEQ ID NO 26
<211> LENGTH: 26
<212> TYPE: DNA
<213> ORGANISM: Artificial Sequence
<220> FEATURE:
<223> OTHER INFORMATION: synthetic DAT marker for dopaminergic neuron
      cells PCR amplification primer

<400> SEQUENCE: 26
actaaagtgg ctgcaagctg accagg                                           26

<210> SEQ ID NO 27
<211> LENGTH: 26
<212> TYPE: DNA
<213> ORGANISM: Artificial Sequence
<220> FEATURE:
<223> OTHER INFORMATION: synthetic Lmx1a marker for dopaminergic neuron
      proliferative progenitor cells, postmitotic
      dopaminergic neuron progenitor cells and
      dopaminergic neurons PCR amplification primer

<400> SEQUENCE: 27
tggttcaggt gtggttccag aaccag                                           26

<210> SEQ ID NO 28
<211> LENGTH: 26
<212> TYPE: DNA
```

```
<213> ORGANISM: Artificial Sequence
<220> FEATURE:
<223> OTHER INFORMATION: synthetic Lmx1a marker for dopaminergic neuron
      proliferative progenitor cells, postmitotic
      dopaminergic neuron progenitor cells and
      dopaminergic neurons PCR amplification primer

<400> SEQUENCE: 28
tctgaggttg ccaggaagca gtctcc                                        26

<210> SEQ ID NO 29
<211> LENGTH: 26
<212> TYPE: DNA
<213> ORGANISM: Artificial Sequence
<220> FEATURE:
<223> OTHER INFORMATION: synthetic Nato3 marker for dopaminergic neuron
      proliferative progenitor cells PCR amplification
      primer

<400> SEQUENCE: 29
cctgggaaga ctgtcgcagt ttgatg                                        26

<210> SEQ ID NO 30
<211> LENGTH: 26
<212> TYPE: DNA
<213> ORGANISM: Artificial Sequence
<220> FEATURE:
<223> OTHER INFORMATION: synthetic Nato3 marker for dopaminergic neuron
      proliferative progenitor cells PCR amplification
      primer

<400> SEQUENCE: 30
gaaggcctcg tttaggttga acatcc                                        26

<210> SEQ ID NO 31
<211> LENGTH: 26
<212> TYPE: DNA
<213> ORGANISM: Artificial Sequence
<220> FEATURE:
<223> OTHER INFORMATION: synthetic Nato3 marker for dopaminergic neuron
      proliferative progenitor cells PCR amplification
      primer for in situ hybridization

<400> SEQUENCE: 31
atcggcagct atgccattcc tgcaag                                        26

<210> SEQ ID NO 32
<211> LENGTH: 26
<212> TYPE: DNA
<213> ORGANISM: Artificial Sequence
<220> FEATURE:
<223> OTHER INFORMATION: synthetic Nato3 marker for dopaminergic neuron
      proliferative progenitor cells PCR amplification
      primer for in situ hybridization

<400> SEQUENCE: 32
tgctccaagc aagaagctct aactcc                                        26

<210> SEQ ID NO 33
<211> LENGTH: 26
<212> TYPE: DNA
<213> ORGANISM: Artificial Sequence
<220> FEATURE:
<223> OTHER INFORMATION: synthetic tyrosine hydroxylase (TH) marker for
      postmitotic dopaminergic neuron precursor cells
      PCR amplification primer for in situ hybridization

<400> SEQUENCE: 33
gctgtcacgt ccccaaggtt cattgg                                        26
```

-continued

<210> SEQ ID NO 34
<211> LENGTH: 26
<212> TYPE: DNA
<213> ORGANISM: Artificial Sequence
<220> FEATURE:
<223> OTHER INFORMATION: synthetic tyrosine hydroxylase (TH) marker for
    postmitotic dopaminergic neuron precursor cells
    PCR amplification primer for in situ hybridization

<400> SEQUENCE: 34
ggagcgcatg cagtagtaag atgtgg                                         26

<210> SEQ ID NO 35
<211> LENGTH: 26
<212> TYPE: DNA
<213> ORGANISM: Artificial Sequence
<220> FEATURE:
<223> OTHER INFORMATION: synthetic Nurr1 marker for postmitotic
    dopaminergic neuron precursor cells PCR
    amplification primer for in situ hybridization

<400> SEQUENCE: 35
catatgatcg agcagaggaa gacacc                                         26

<210> SEQ ID NO 36
<211> LENGTH: 26
<212> TYPE: DNA
<213> ORGANISM: Artificial Sequence
<220> FEATURE:
<223> OTHER INFORMATION: synthetic Nurr1 marker for postmitotic
    dopaminergic neuron precursor cells PCR
    amplification primer for in situ hybridization

<400> SEQUENCE: 36
agtgcgaaca ccgtagtgct gacagg                                         26

<210> SEQ ID NO 37
<211> LENGTH: 26
<212> TYPE: DNA
<213> ORGANISM: Artificial Sequence
<220> FEATURE:
<223> OTHER INFORMATION: synthetic tyrosine hydroxylase (TH) marker for
    postmitotic dopaminergic neuron precursor cells
    RT-PCR amplification primer

<400> SEQUENCE: 37
gttcccaagg aaagtgtcag agttgg                                         26

<210> SEQ ID NO 38
<211> LENGTH: 26
<212> TYPE: DNA
<213> ORGANISM: Artificial Sequence
<220> FEATURE:
<223> OTHER INFORMATION: synthetic tyrosine hydroxylase (TH) marker for
    postmitotic dopaminergic neuron precursor cells
    RT-PCR amplification primer

<400> SEQUENCE: 38
gaagctggaa agcctccagg tgttcc                                         26

<210> SEQ ID NO 39
<211> LENGTH: 26
<212> TYPE: DNA
<213> ORGANISM: Artificial Sequence
<220> FEATURE:
<223> OTHER INFORMATION: synthetic DAT marker for postmitotic
    dopaminergic neuron precursor cells RT-PCR amplification primer

```
<400> SEQUENCE: 39
ctccgagcag acaccatgac cttagc                                            26

<210> SEQ ID NO 40
<211> LENGTH: 26
<212> TYPE: DNA
<213> ORGANISM: Artificial Sequence
<220> FEATURE:
<223> OTHER INFORMATION: synthetic DAT marker for postmitotic
      dopaminergic neuron precursor cells RT-PCR amplification primer

<400> SEQUENCE: 40
aggagtaggg cttgtctccc aacctg                                            26

<210> SEQ ID NO 41
<211> LENGTH: 26
<212> TYPE: DNA
<213> ORGANISM: Artificial Sequence
<220> FEATURE:
<223> OTHER INFORMATION: synthetic Nurr1 marker for postmitotic
      dopaminergic neuron precursor cells RT-PCR
      amplification primer

<400> SEQUENCE: 41
cactcctgtg tctagctgcc agatgc                                            26

<210> SEQ ID NO 42
<211> LENGTH: 26
<212> TYPE: DNA
<213> ORGANISM: Artificial Sequence
<220> FEATURE:
<223> OTHER INFORMATION: synthetic Nurr1 marker for postmitotic
      dopaminergic neuron precursor cells RT-PCR
      amplification primer

<400> SEQUENCE: 42
agtgcgaaca ccgtagtgct gacagg                                            26

<210> SEQ ID NO 43
<211> LENGTH: 26
<212> TYPE: DNA
<213> ORGANISM: Artificial Sequence
<220> FEATURE:
<223> OTHER INFORMATION: synthetic Ptx3 marker for postmitotic
      dopaminergic neuron precursor cells RT-PCR amplification primer

<400> SEQUENCE: 43
tgagccgcag gtctgtggat ccatcc                                            26

<210> SEQ ID NO 44
<211> LENGTH: 26
<212> TYPE: DNA
<213> ORGANISM: Artificial Sequence
<220> FEATURE:
<223> OTHER INFORMATION: synthetic Ptx3 marker for postmitotic
      dopaminergic neuron precursor cells RT-PCR amplification primer

<400> SEQUENCE: 44
tccctgttcc tggccttagt cctagg                                            26

<210> SEQ ID NO 45
<211> LENGTH: 26
<212> TYPE: DNA
<213> ORGANISM: Artificial Sequence
<220> FEATURE:
<223> OTHER INFORMATION: synthetic En1 marker for postmitotic
      dopaminergic neuron precursor cells RT-PCR amplification primer
```

```
<400> SEQUENCE: 45
atcctccgag tggacattca catagg                                          26

<210> SEQ ID NO 46
<211> LENGTH: 27
<212> TYPE: DNA
<213> ORGANISM: Artificial Sequence
<220> FEATURE:
<223> OTHER INFORMATION: synthetic En1 marker for postmitotic
      dopaminergic neuron precursor cells RT-PCR amplification primer

<400> SEQUENCE: 46
atgtccagca aatagagatc gctacac                                         27
```